(12) United States Patent
Cauley, III et al.

(10) Patent No.: US 9,399,215 B2
(45) Date of Patent: Jul. 26, 2016

(54) SAMPLE HOLDER WITH A WELL HAVING A WICKING PROMOTER

(71) Applicant: Bio-Rad Laboratories, Inc., Hercules, CA (US)

(72) Inventors: Thomas H. Cauley, III, Pleasanton, CA (US); Luc Bousse, Los Altos, CA (US); Jonathan Petersen, Sunnyvale, CA (US); Kevin D. Ness, Pleasanton, CA (US); Steven Romine, Vacaville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 526 days.

(21) Appl. No.: 13/863,231

(22) Filed: Apr. 15, 2013

(65) Prior Publication Data

US 2013/0269452 A1    Oct. 17, 2013

Related U.S. Application Data

(60) Provisional application No. 61/624,199, filed on Apr. 13, 2012.

(51) Int. Cl.
*B01L 3/00* (2006.01)
*G01N 1/00* (2006.01)
*B32B 38/00* (2006.01)

(52) U.S. Cl.
CPC ..... *B01L 3/502715* (2013.01); *B01L 3/502707* (2013.01); *B01L 3/502746* (2013.01); *B32B 38/0012* (2013.01); *G01N 1/00* (2013.01); *B01L 3/502784* (2013.01); *B01L 2200/027* (2013.01); *B01L 2200/0673* (2013.01); *B01L 2300/161* (2013.01); *B01L 2400/0406* (2013.01); *B01L 2400/086* (2013.01); *B01L 2400/088* (2013.01); *Y10T 156/10* (2015.01); *Y10T 156/1002* (2015.01)

(58) Field of Classification Search
CPC ..................... B01L 3/502715; B01L 3/502746
See application file for complete search history.

(56) References Cited

U.S. PATENT DOCUMENTS

| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |

(Continued)

FOREIGN PATENT DOCUMENTS

| EP | 1 522 582 A2 | 4/2005 |
| EP | 1 522 582 B1 | 4/2007 |

(Continued)

OTHER PUBLICATIONS

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

(Continued)

*Primary Examiner* — Paul West
(74) *Attorney, Agent, or Firm* — Kolisch Hartwell, P.C.

(57) ABSTRACT

Sample holding system, including methods and apparatus, including a holder defining a well having a wicking promoter that encourages flow of a sample to the bottom of the well. Methods of making and using the holder are also disclosed.

14 Claims, 19 Drawing Sheets

(56) References Cited

U.S. PATENT DOCUMENTS

| | | |
|---|---|---|
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0171170 A1 | 9/2004 | Sandell |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |

(56) References Cited

U.S. PATENT DOCUMENTS

| | | |
|---|---|---|
| 2005/0227264 A1 | 10/2005 | Nobile et al. |
| 2005/0236317 A1 | 10/2005 | Desilets et al. |
| 2005/0239192 A1 | 10/2005 | Nasarabadi et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0064781 A1 | 3/2010 | Cherubini et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12337 | 2/2001 |
| WO | 02/23163 | 3/2002 |

(56) References Cited

FOREIGN PATENT DOCUMENTS

| WO | 02/060584 | 8/2002 |
|---|---|---|
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011028760 A2 | 3/2011 |
| WO | 2011/079176 | 6/2011 |

OTHER PUBLICATIONS

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL Struct. vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al., "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

Goldschmidt GmbH, "Abil® EM 90 Emulsifier for the formulation of cosmetic W/O creams and lotions," degussa. creating essentials brochure, pp. 1-7, May 2003.

Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).

R. G. Rutledge et al., "Mathematics of quantitative kinetic PCR and the application of standard curves," Nucleic Acids Research, vol. 31, No. 16, pp. 1-6, (2003).

Chunming Ding et al., "Direct molecular haplotyping of long-range genomic DNA with M1-PCR," PNAS, vol. 100, No. 13, pp. 7449-7453, Jun. 24, 2003.

(56) References Cited

OTHER PUBLICATIONS

Devin Dressman et al., "Transforming single DNA molecules into fluorescent magnetic particles for detection and enumeration of genetic variations," PNAS, vol. 100, No. 15, Jul. 22, 2003.

Ulf Landegren et al., "Padlock and proximity probes for in situ and array-based analyses: tools for the post-genomic era," Comp. Funct. Genom, vol. 4, pp. 525-530, (2003).

Gudrun Pohl et al., "Principle and applications of digital PCR" review, www.future-drugs.com, Expert Rev. Mol. Diagn. 4(1), pp. 41-47, (2004).

Groff M. Schroeder et al., "Introduction to Flow Cytometry" version 5.1, 182 pgs. (2004).

Stéphane Swillens et al., "Instant evaluation of the absolute initial number of cDNA copies from a single real-time PCR curve," Nucleic Acids Research, vol. 32, No. 6, pp. 1-6, (2004).

Mats Gullberg et al., "Cytokine detection by antibody-based proximity ligation," PNAS, vol. 101, No. 22, pp. 8420-8424, Jun. 1, 2004.

Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.

R. G. Rutledge, "Sigmoidal curve-fitting redefines quantitative real-time PCR with the prospective of developing automated high-throughput applications," Nucleic Acids Research. vol. 32, No. 22, pp. 1-8, (2004).

L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.

Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.

James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).

Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.

Anna Musyanovych et al., "Miniemulsion Droplets as Single Molecule Nanoreactors for Polymerase Chain Reaction," Biomacromolecules, vol. 6, No. 4, pp. 1824-1828, (2005).

Max Chabert et al., "Droplet fusion by alternating current (AC) field electrocoalescence in microchannels," Electrophoresis, vol. 26, pp. 3706-3715, (2005).

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

Marcel Margulies et al., "Genome sequencing in microfabricated high-density picolitre reactors," Nature, vol. 437, 51 pgs., Sep. 15, 2005.

Kristofer J. Thurecht et al., "Investigation of spontaneous microemulsion formation in supercritical carbon dioxide using high-pressure NMR," Journal of Supercritical Fluids, vol. 38, pp. 111-118, (2006).

Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).

Piotr Garstecki et al., "Formation of droplets and bubbles in a microfluidic T-junction—scaling and mechanism of break-up," Lab on a Chip, vol. 6, pp. 437-446, (2006).

Darren R. Link et al., "Electric Control of Droplets in Microfluidic Devices," Angewandte Chemie Int. Ed., vol. 45, pp. 2556-2560, (2006).

Peter Fielden et al., "Micro-Droplet Technology for High Throughout Systems and Methods," 1 pg., Mar. 8, 2006.

David Emerson et al., "Microfluidic Modelling Activities at C3M," Centre for Microfluidics & Microsystems Modelling, Daresbury Laboratory, pp. 1-26, May 15, 2006.

Richard Williams et al., "Amplification of complex gene libraries by emulsion PCR," Nature Methods, vol. 3, No. 7, pp. 545-550, Jul. 2006.

John H. Leamon et al., "Overview: methods and applications for droplet compartmentalization of biology," Nature Methods, vol. 3, No. 7, pp. 541-543, Jul. 2006.

Andrew D. Griffiths et al., "Miniaturising the laboratory in emulsion droplets," Trends in Biotechnology, vol. 24, No. 9, pp. 395-402, Jul. 14, 2006.

Jian-Bing Fan et al., "Highly parallel genomic assays," Nature Reviews/Genetics, vol. 7, pp. 632-644, Aug. 2006.

Jonas Jarvius et al., "Digital quantification using amplified single-molecule detection," Nature Methods, vol. 3, No. 9, pp. 15 pgs, Sep. 2006.

Kan Liu et al., "Droplet-based synthetic method using microflow focusing and droplet fusion," Microfluid Nanfluid, vol. 3, pp. 239-243, (2007), published online Sep. 22, 2006.

Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.

Kristofer J. Thurecht et al., "Kinetics of Enzymatic Ring-Opening Polymerization of ε-Caprolactone in Supercritical Carbon Dioxide," Macromolecules, vol. 39, pp. 7967-7972, (2006).

Machiko Hori et al., "Uniform amplification of multiple DNAs by emulsion PCR," Biochemical and Biophysical Research Communications, vol. 352, pp. 323-328, (2007).

Frank Diehl et al., "Digital quantification of mutant DNA in cancer patients," Current Opinion in Oncology, vol. 19, pp. 36-42, (2007).

Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

S. Mohr et al., "Numerical and experimental study of a droplet-based PCR chip," Microfluid Nanofluid, vol. 3, pp. 611-621, (2007).

Sigrun M. Gustafsdottir et al., "In vitro analysis of DNA-protein interactions by proximity ligation," PNAS, vol. 104, No. 9, pp. 3067-3072, Feb. 27, 2007.

Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.

Charles N. Baroud et al., "Thermocapillary valve for droplet production and sorting," Physical Review E 75, 046302, pp. 046302-1-046302-5, Apr. 5, 2007.

Qinyu Ge et al., "Emulsion PCR-based method to detect Y chromosome microdeletions," Analytical Biochemistry, vol. 367, pp. 173-178, May 10, 2007.

Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.

Y. M. Dennis Lo et al., "Digital PCR for the molecular detection of fetal chromosomal aneuploidy," PNAS, vol. 104, No. 32, pp. 13116-13121, Aug. 7, 2007.

Dayong Jin et al., "Practical Time-Gated Luminescence Flow Cytometry. II: Experimental Evaluation Using UV LED Excitation," Cytometry Part A • 71A, pp. 797-808, Aug. 24, 2007.

Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.

Nathan Blow, "PCR's next frontier," Nature Methods, vol. 4, No. 10, pp. 869-875, Oct. 2007.

Nicole Pamme, "Continuous flow separations in microfluidic devices," Lab on a Chip, vol. 7, pp. 1644-1659, Nov. 2, 2007.

N. Reginald Beer et al., "On-Chip, Real-Time, Single-Copy Polymerase Chain Reaction in Picoliter Droplets," Analytical Chemistry, vol. 79, No. 22, pp. 8471-8475, Nov. 15, 2007.

(56) References Cited

OTHER PUBLICATIONS

Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).

Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semisolid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
THINXXS Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS ONE, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
LABSMITH, "Microfluid Components" webpage, downloaded Jul. 11, 2012.
LABSMITH, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
Blaine R. Copenheaver, Authorized Officer, International Searching Authority, U.S. Patent and Trademark Office, "International Search Report" in connection with related PCT Patent Application No. PCT/US2013/036649, dated Aug. 5, 2013, 3 pages.
Blaine R. Copenheaver, Authorized Officer, International Searching Authority, U.S. Patent and Trademark Office, "Written Opinion of the International Searching Authority" in connection with related PCT Patent Application No. PCT/US2013/036649, dated Aug. 5, 2013, 6 pages.

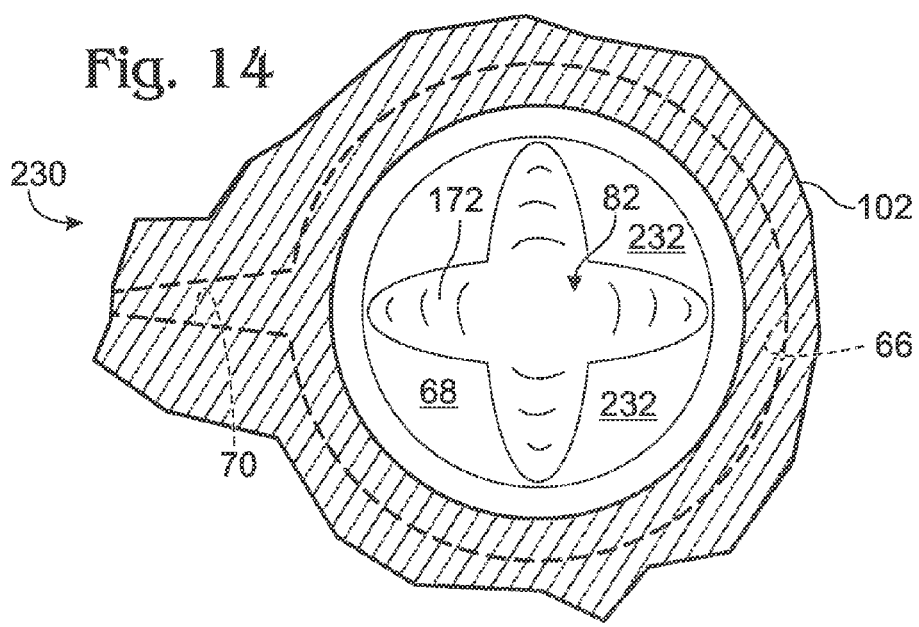
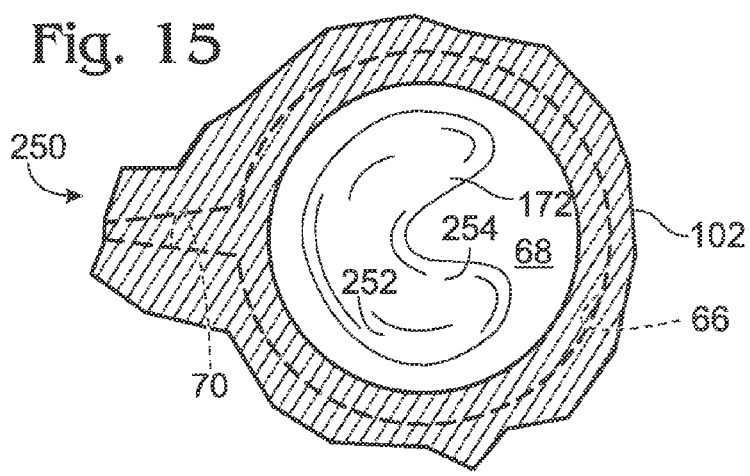
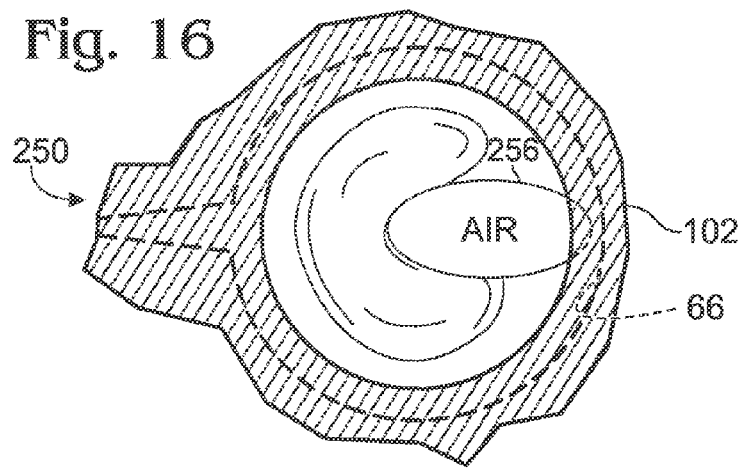

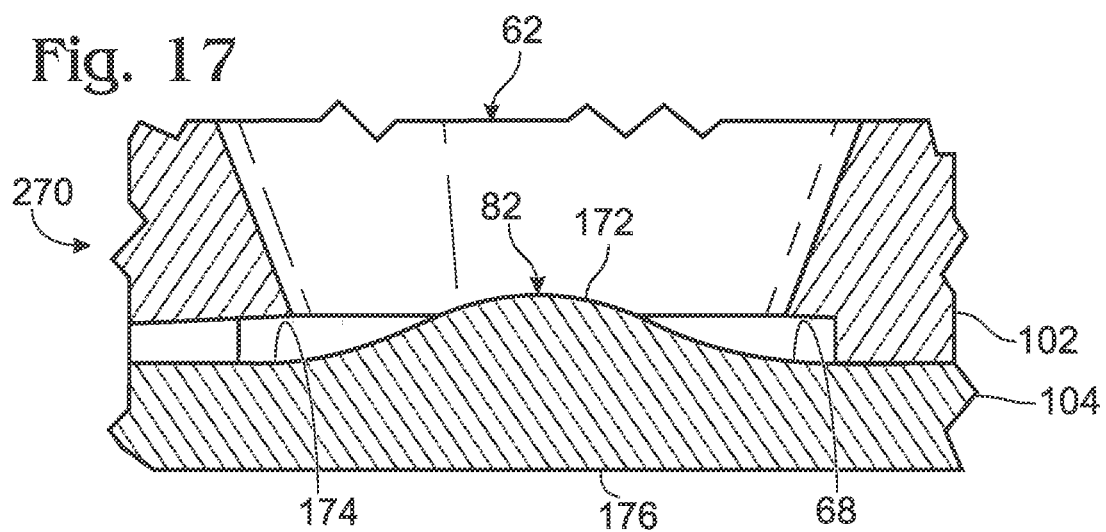
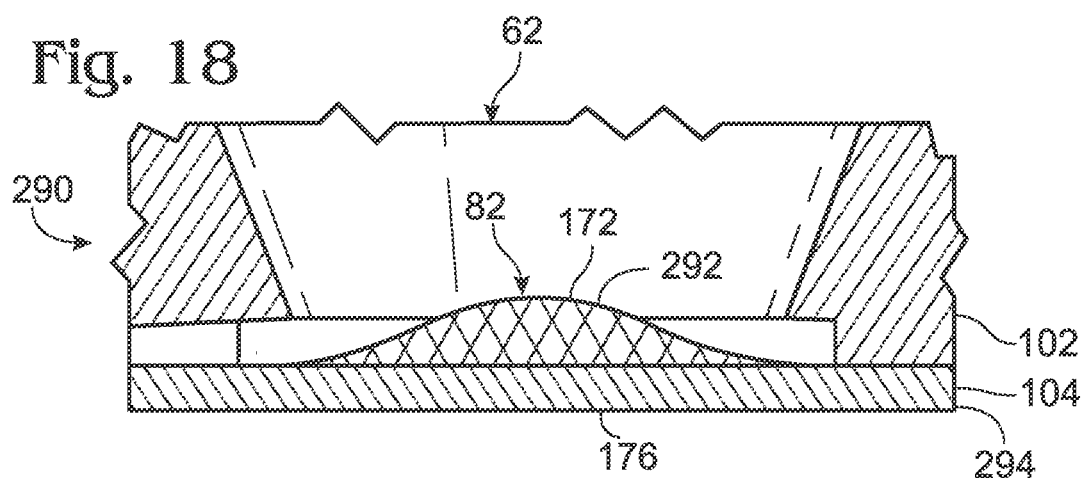

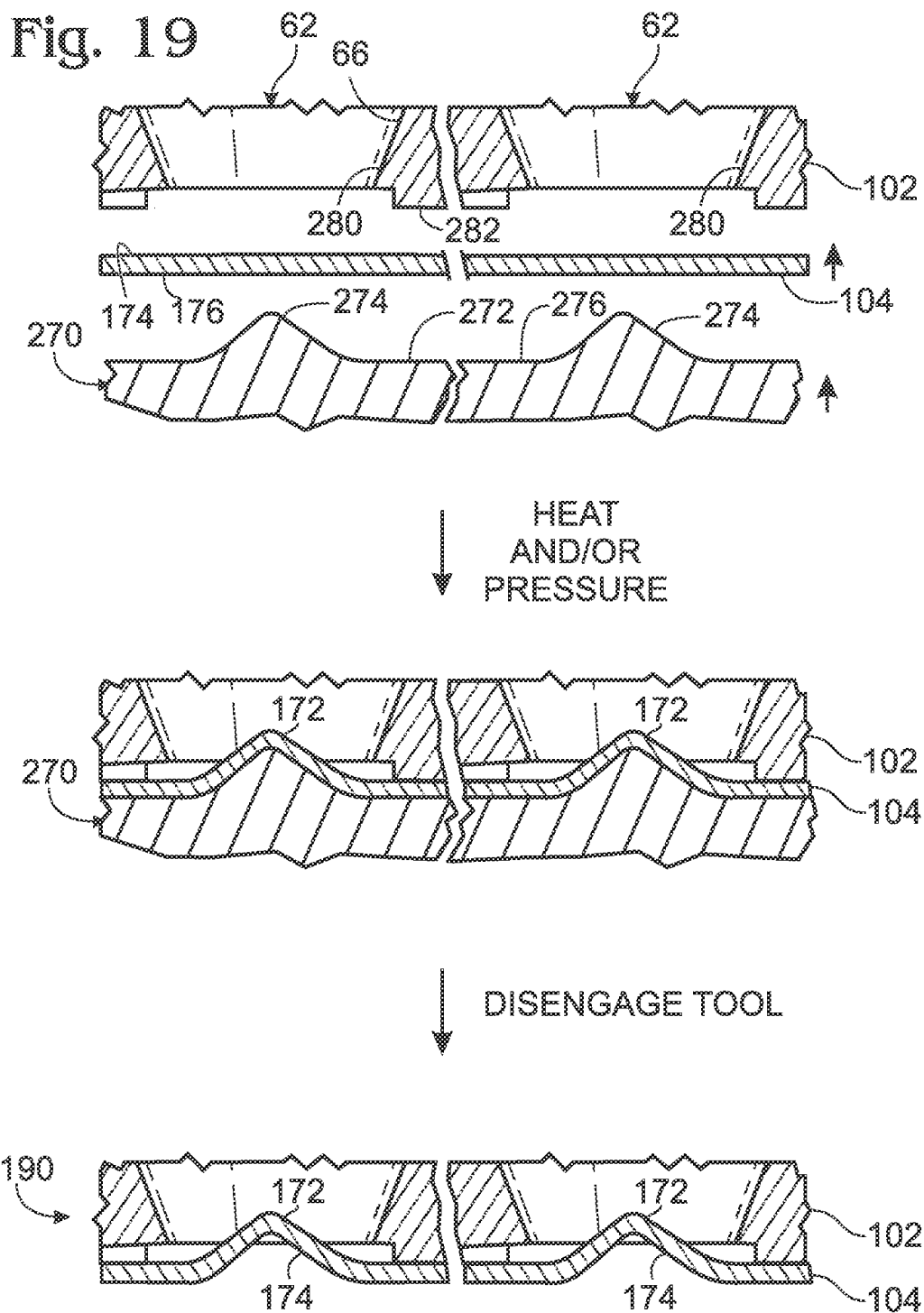

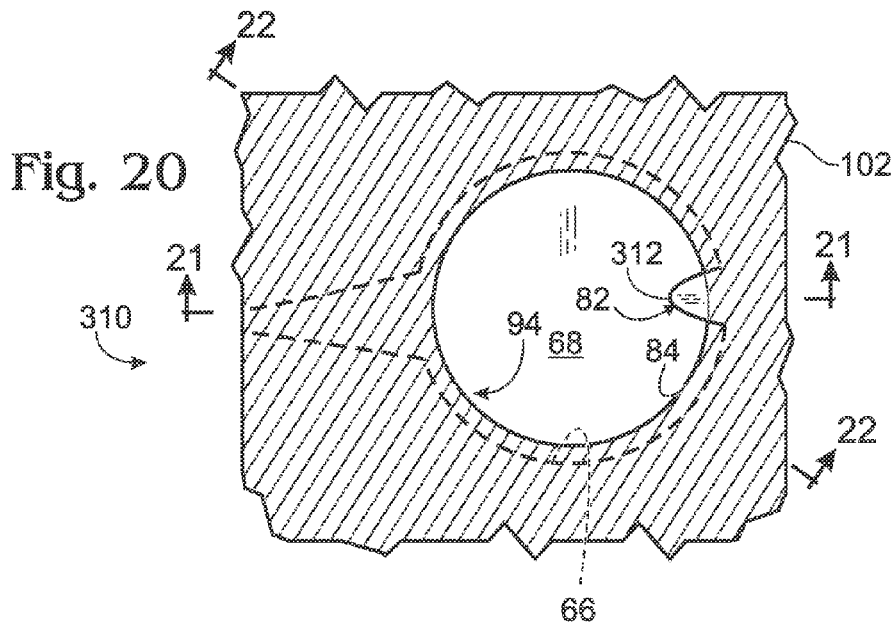
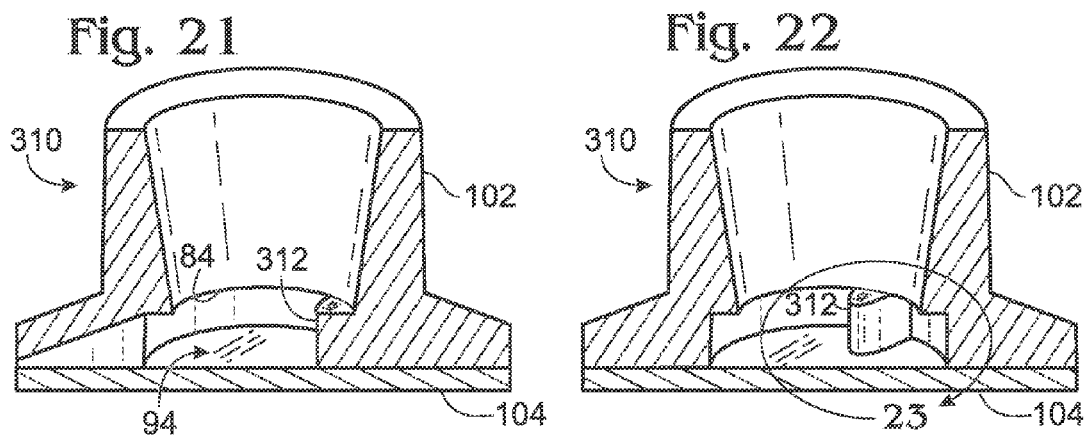
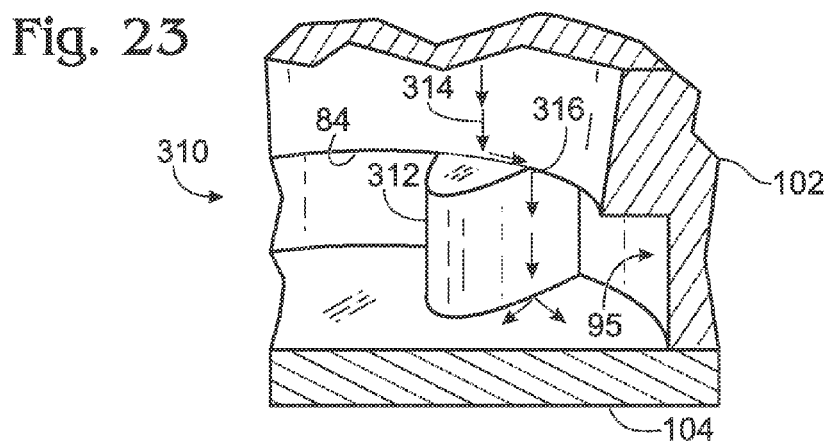

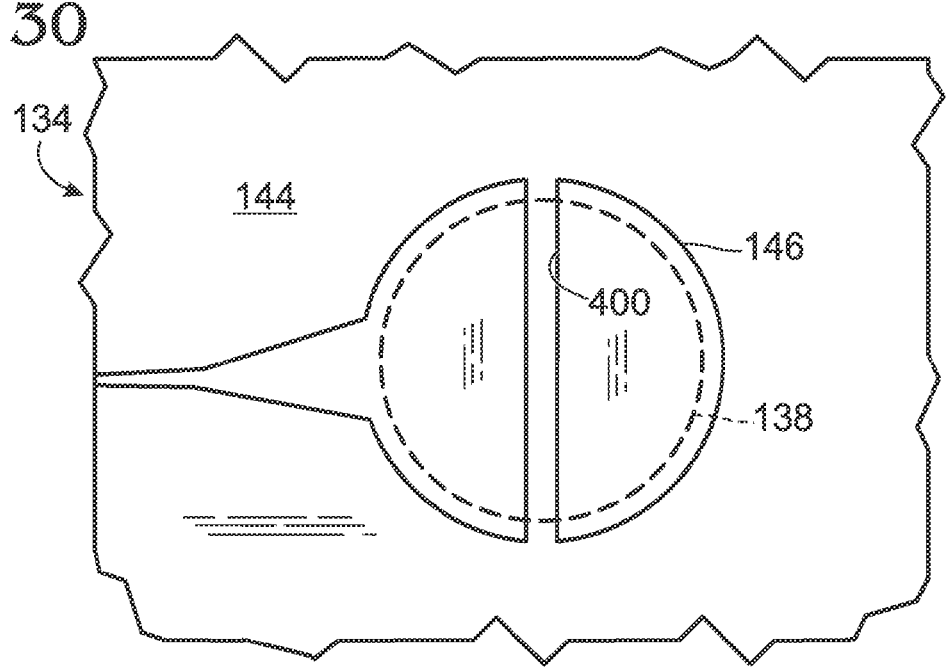
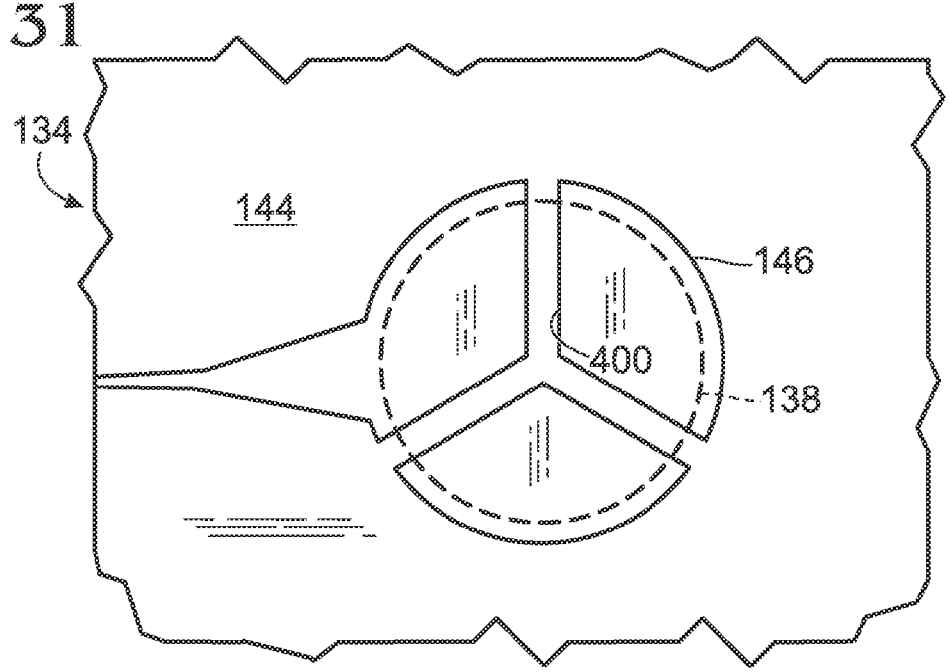

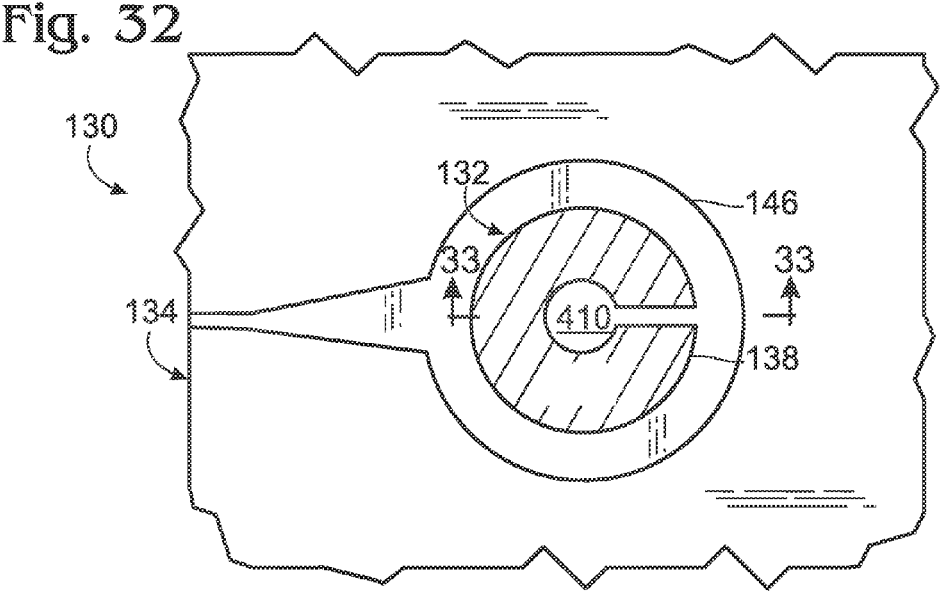
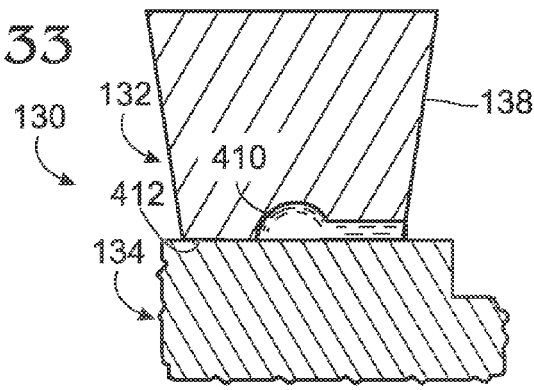
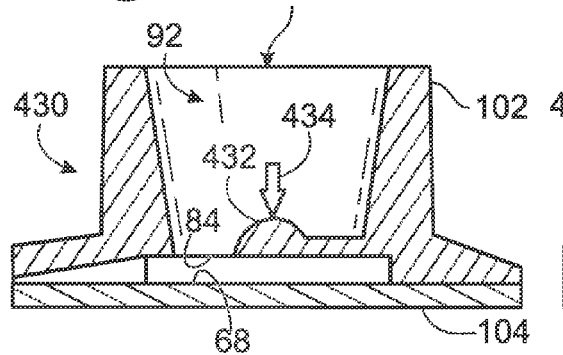
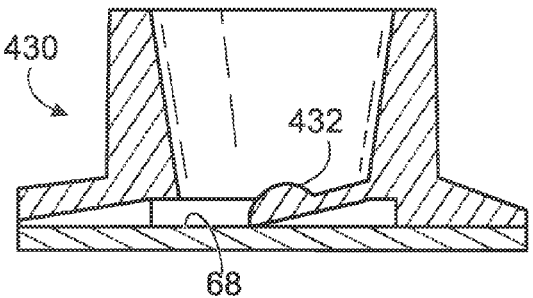

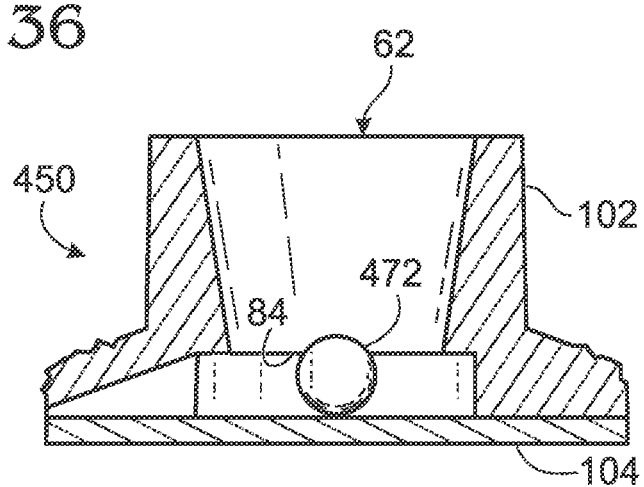
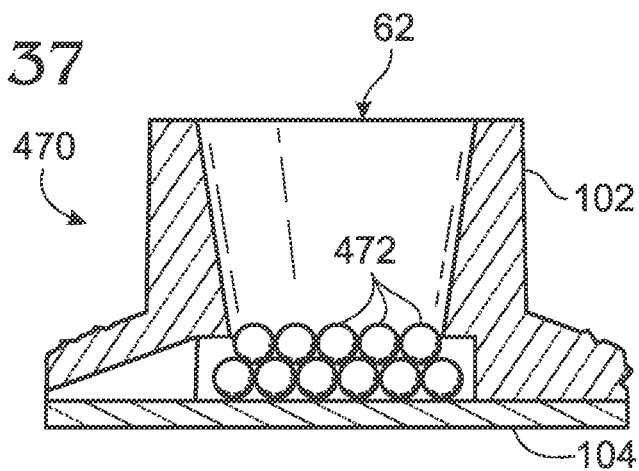

SAMPLE HOLDER WITH A WELL HAVING A WICKING PROMOTER

CROSS-REFERENCE TO PRIORITY APPLICATION

This application is based upon and claims the benefit under 35 U.S.C. §119(e) of U.S. Provisional Patent Application Ser. No. 61/624,199, filed Apr. 13, 2012, which is incorporated herein by reference in its entirety for all purposes.

CROSS-REFERENCES TO OTHER MATERIALS

This application incorporates by reference in their entireties for all purposes the following patent documents: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; and U.S. Patent Application Publication No. 2012/0152369 A1, published Jun. 21, 2012.

INTRODUCTION

Surface tension can hamper manipulation of small-volume liquid samples in situations where gravitational forces play only a minor role. For example, an aqueous sample dispensed into a well of a sample holder may not flow to the bottom of the well if the well is shaped to have an abrupt change in surface contour forming an edge intermediate the top and the bottom of the well. The sample may travel down to the edge and then stop, with the sample being incapable of wicking past the edge because the contact angle of the sample on the well surface is too large. The sample thus may be pinned at an incorrectly loaded position, with air trapped between the sample and the well bottom. If the well communicates with a channel near the bottom of the well, the sample may fail to enter the channel, preventing any intended sample processing in the channel or downstream thereof.

Whether a sample is pinned or reaches the bottom of a well can be affected by variations in sample dispensing. For example, if a sample is dispensed manually into a series of wells with a pipette, the position of the pipette tip and the ejection velocity of the sample from the pipette may vary substantially from well to well, and from user to user, thereby creating unreliability in sample loading. It would advantageous for a sample holder to have a well design that encourages sample to flow to a correctly loaded position, from various receiving locations in the well, and with fewer limitations on the pipette used.

Problems with unintended sample pinning could be overcome, in some cases, by increasing the well diameter to reduce the effect of surface tension relative to gravity. However, since a larger well has a greater surface area, increases in well size are generally undesirable due to the increased amount of residual sample that remains on the surface of the well after the well is emptied of sample. Also, increasing the footprint of the well can make a sample holder less compact by reducing the number of wells that can fit on a holder of a given size.

Improved sample holders are needed to receive small volumes of sample with less sample pinning in an incorrect loading configuration.

SUMMARY

The present disclosure provides a sample holding system, including methods and apparatus, including a holder defining a well having a wicking promoter that encourages flow of a sample to the bottom of the well. Methods of making and using the holder are also disclosed.

BRIEF DESCRIPTION OF THE DRAWINGS

FIG. 14 is a fragmentary sectional view of still another exemplary sample holder defining a well having a floor protrusion for encouraging a sample to wick to the bottom of a well, with the view taken generally as in FIG. 13, in accordance with aspects of the present disclosure.

FIG. 15 is a fragmentary sectional view of still yet another exemplary sample holder defining a well having a floor protrusion for encouraging a sample to wick to the bottom of a well, in accordance with aspects of the present disclosure.

FIG. 16 is a fragmentary sectional view of the sample holder of FIG. 15, taken as in FIG. 15 in the presence of a residual air bubble to illustrate how the floor protrusion can trap the air bubble in a pocket formed by the protrusion, in accordance with aspects of the present disclosure.

FIG. 17 is a fragmentary sectional view of an exemplary sample holder taken generally as in FIG. 7 and defining a well having a floor protrusion formed without an opposing dimple, in accordance with aspects of the present disclosure.

FIG. 18 is a fragmentary sectional view of an exemplary sample holder taken generally as in FIG. 7 and defining a well having a floor protrusion formed as a mass attached to or deposited on a sheet of a material, in accordance with aspects of the present disclosure.

FIG. 19 is a flow diagram illustrating selected aspects of an exemplary method of constructing a sample holder defining a well having a floor protrusion, in accordance with aspects of the present disclosure.

FIG. 20 is a fragmentary sectional view of an exemplary sample holder taken generally as in FIG. 13 and defining a well having a wicking promoter structured as a side wall protrusion, in accordance with aspects of the present disclosure.

FIG. 21 is a fragmentary sectional view of the sample holder of FIG. 20, taken generally along line 21-21 of FIG. 20.

FIG. 22 is another fragmentary sectional view of the sample holder of FIG. 20, taken generally along line 22-22 of FIG. 20.

FIG. 23 is a magnified view of a portion of the sample holder of FIG. 20, taken generally at the region indicated at "23" in FIG. 22 and illustrating an exemplary wicking pathway for fluid travel to the bottom of the well, in accordance with aspects of the present disclosure.

FIG. 30 is a fragmentary plan view of an exemplary die member that may be used as part of a mold to form a well having a side wall protrusion that acts as a wicking promoter structured as a transverse ridge spanning the well crosswise, in accordance with aspects of the present disclosure.

FIG. 31 is a fragmentary plan view of an exemplary die member that may be used as part of a mold to form a well having a side wall protrusion that acts as wicking promoter structured as series of intersecting ridges extending radially inward from the perimeter of the well, in accordance with aspects of the present disclosure.

FIG. 32 is a fragmentary plan view of an exemplary mold for molding an upper member of a sample holder, with the mold viewed generally as in FIG. 5 and including a pin with a cavity formed in a distal end surface of the pin to mold an elevated, cantilevered side wall protrusion in a well, in accordance with aspects of the present disclosure.

FIG. 33 is a fragmentary sectional view of the mold of FIG. 32, taken generally along line 33-33 of FIG. 32.

FIG. 34 is a fragmentary sectional view of an exemplary sample holder formed using the mold of FIGS. 32 and 33, before the side wall protrusion has been positioned in contact with the floor of the well, in accordance with aspects of the present disclosure.

FIG. 35 is a fragmentary sectional view of the sample holder of FIG. 34 after the protrusion has been deformed into contact with the floor of the well, in accordance with aspects of the present disclosure.

FIG. 36 is a fragmentary sectional view of an exemplary sample holder defining a well containing a bead that functions as a wicking promoter, in accordance with aspects of the present disclosure.

FIG. 37 is a fragmentary sectional view of an exemplary sample holder defining a well containing a plurality of beads that function collectively as a wicking promoter, in accordance with aspects of the present disclosure.

DETAILED DESCRIPTION

Figure 1:
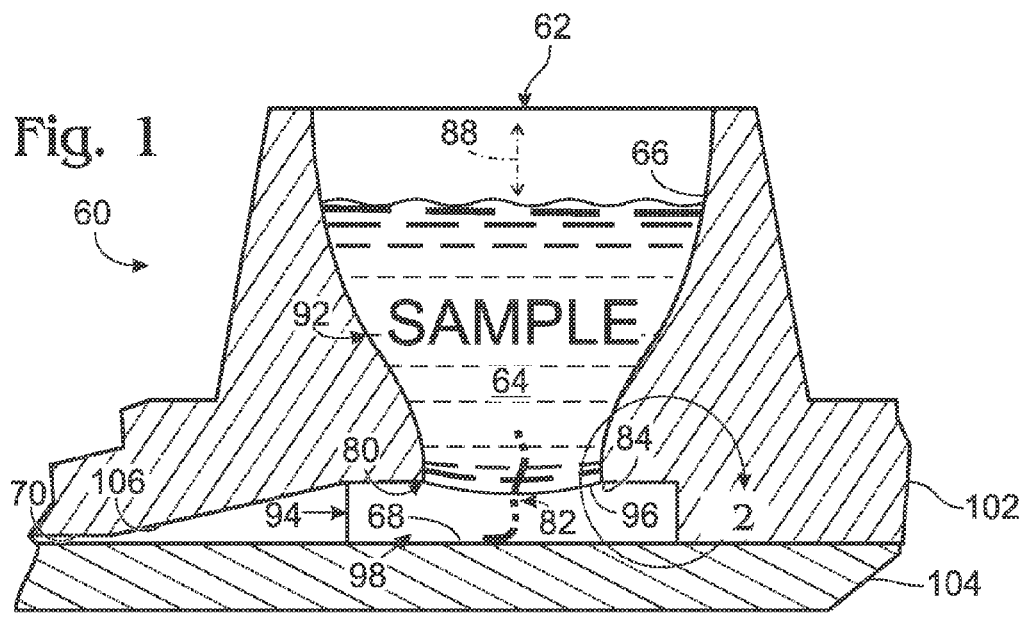
FIG. 1 is a fragmentary sectional view of an exemplary sample holder defining a well having a wicking impediment and containing an aqueous sample pinned above the bottom of the well by the impediment, in accordance with aspects of the present disclosure.

The present disclosure provides a sample holding system, including methods and apparatus, including a holder defining a well having a wicking promoter that encourages flow of a sample to the bottom of the well. Methods of making and using the holder are also disclosed.

A device for holding a sample of small volume is provided. The device may comprise a holder including an upper member attached to a lower member to form a well having a side wall and a floor. The side wall may be created by a wicking impediment conceptually dividing the well into an upper region and a lower region. The well may include a wicking promoter adapted to encourage a sample to wick from the upper region to the lower region.

Another device for holding a sample of small volume is provided. The device may comprise a holder including an upper member attached to a lower member to form a well having a side wall and a floor. The side wall may create a distinct edge or convex corner that extends about a central vertical axis of the well to conceptually divide the well into an upper region and a lower region and capable of acting as an impediment to wicking of a sample from the upper region to the lower region. The well may include a protrusion defined by the upper member, the lower member, or both the upper member and the lower member collectively, and adapted to promote wicking of a sample into the lower region from the upper region.

A method of using a device for holding a sample of small volume is provided. The method may comprise dispensing an aqueous sample into a well of the device.

A method of making a device for holding a sample is provided. In the method, an upper member may be provided. The upper member may define at least one through-hole having a surface forming a distinct edge or convex corner that extends about a central axis of the through-hole and that conceptually divides the through-hole into an upper region and a lower region. A well may be created. The well may have a lower member attached to an underside of the upper member, with the surface of the through-hole forming a side wall of the well and the lower member forming a floor of the well. The upper member, the lower member, or both the upper member and the lower member collectively, may define a protrusion adapted to promote wicking of a fluid sample into the lower region from the upper region.

Further aspects of the present disclosure are presented in the following sections: (I) overview of an exemplary sample holder with a wicking impediment, (II) exemplary wicking promoters formed as floor protrusions, (III) exemplary construction of a sample holder with a floor protrusion, (IV) exemplary wicking promoters formed as side wall protrusions, and (V) examples.

I. Overview of an Exemplary Sample Holder with a Wicking Impediment

This section describes an exemplary sample holder defining a well (or reservoir) having a wicking impediment that causes a liquid sample to be pinned in a static configuration at the impediment, without reaching the bottom of the well, and also describes mold structures that can create the wicking impediment through injection molding; see FIGS. 1-5. Related, similar, or identical parts and features of different sample holders and molds are labeled in this and the following sections with the same identifying numbers.

Figure 2:
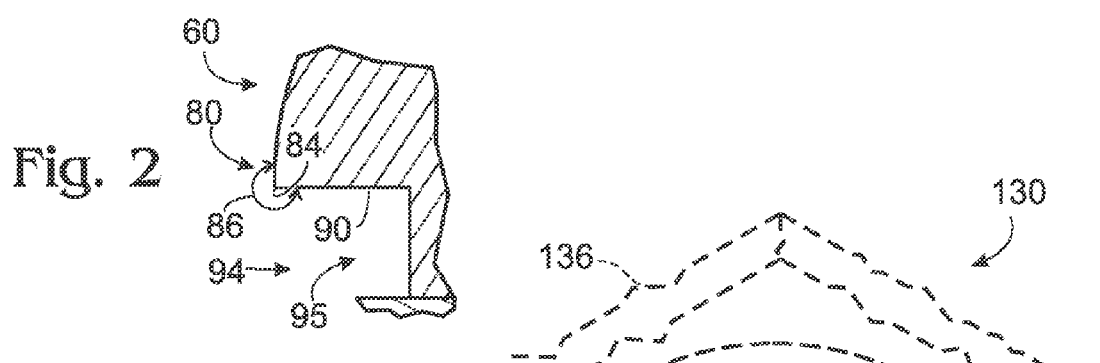
FIG. 2 is a magnified view of the sample holder of FIG. 1, taken generally at the region indicated at "2" in FIG. 1.

FIGS. 1 and 2 show an exemplary sample holder or container 60 having at least one well or reservoir 62 for receiving and containing a small volume of a liquid sample, such as an aqueous sample 64. The fluid capacity of well 62 may be less than about 1000, 250, 100, 50, 20, or 10 microliters, among others. Well 62 may be bounded by a side surface or side wall 66 and a bottom surface or floor 68 that collectively define a compartment for receiving fluid. The top of the well may be open, particularly during sample loading, and/or may have a ceiling (e.g., provided by a removable cover), particularly after sample loading.

The well may be in fluid communication with a channel 70 that permits sample egress from the well. Channel 70 may taper in height and/or width (and/or diameter) as it extends away from the well, such as tapering by a factor of at least about two in height and/or width. In other embodiments, a plurality of channels 70 may communicate separately with the well.

Well 62 may include a wicking impediment 80, which may be formed by side wall 66. The wicking impediment may be any surface feature that inhibits or blocks travel of a fluid along a surface by wicking. The present disclosure provides a wicking promoter 82 (shown here in phantom) that encourages flow of fluid past the wicking impediment to the bottom of the well. In exemplary embodiments, wicking promoter 82 may include at least one protrusion defined by and/or projecting from side wall 66 (i.e., a side wall protrusion) or floor 68 (i.e., a floor protrusion) (see Sections II-IV). In other exemplary embodiments (see Section V), wicking promoter 82 may be provided by one or more added wicking elements, such as one or more beads or fibers contained by well 62, and/or may be created by a surface modification of side wall 66.

Wicking is the flow of a fluid along a surface driven by surface tension, in opposition to a flow-resistive force, such as surface tension, pressure, and/or gravity, among others. The tendency of a fluid to wick along a surface can be characterized by the relationship between (a) adhesive forces between the fluid and the surface and (b) cohesive forces among molecules of the fluid, which results in a contact angle of the fluid on the surface. The contact angle can be measured as the angle formed by a small drop of the fluid in contact with the surface. If the contact angle is above 90 degrees, the fluid resists spreading on the surface and generally does not wick. If the contact angle is less than 90 degrees, the fluid generally wicks and does so with an efficiency inversely related to the size of the contact angle.

Wicking impediment 80 may be formed by an abrupt change in surface contour of side wall 66 that creates a convex corner 84 at a junction between contiguous surface regions that are angled relative to each other (see FIG. 2). The corner, which also or alternatively may be described as a distinct edge or a surface discontinuity, defines an obtuse angle 86. The angle is measured through fluid/air between the angled surface regions and may, for example, be at least about 200, 225, 240, or 270 degrees, among others.

Corner 84 may extend about a central vertical axis 88 defined by the well (see FIG. 1). In some cases, the corner may extend completely around axis 88 on a looped path to form a continuous corner (interchangeably termed a continuous wicking impediment). The looped path (and the corner) may be disposed in a plane.

The well may be undercut adjacent floor 68 to produce a stepped increase in diameter near the floor that creates corner 84 and an overhang 90 adjacent the corner (see FIG. 2). The corner and/or the overhang conceptually divide the well into an upper region 92 and a lower region 94. The upper region begins at the top of the well and ends at corner 84. The lower region begins at corner 84 and/or overhang 90 and ends at the bottom of the well. The upper region may form a majority of the height and/or volume of the well, such as at least about 80%, 90%, 95%, or 98%, among others, of the height and/or volume.

The lower region may define an undercut portion 95 forming a perimeter, optionally ring-shaped, volume of the lower region. The undercut region may be bounded above by overhang 90 and below by a margin of floor 68, and bounded on a radially outward side by side wall 66 below overhang 90. The undercut portion may be open on a radially inward side, with a position defined by a vertical projection of corner 84.

Impediment 80 may prevent sample 64 from wicking into lower region 94 of the well, as shown in FIG. 1. For example, corner 84 may form an obtuse angle that is too large for the sample to wet any part of the lower region of the well past the corner, due to the sample's relatively large contact angle on the surface of the side wall (e.g., greater than about 60, 70, or 80 degrees among others). Surface tension at a lower sample-air interface 96 may be dominant over gravity to hold the sample at a static, elevated position at which the sample spans side wall 66 transversely and is pinned above floor 68 with an air gap 98 separating static interface 96 and floor 68. The meniscus formed by the sample at interface 96 may be convex, planar, or concave based, for example, on well geometry, wettability of the well surface, and surface tension.

Sample pinning prevents or delays entry of the sample into channel 70, thereby rendering the sample holder nonfunctional or at least unreliable for its intended purpose. For surface tension to be dominant, the well may be designed to receive a small volume of sample, with the well having a diameter (generally a minimum diameter measured between diametrically opposed sites of corner 84) of less than about 10, 8, 6, 4, or 2 millimeters, among others.

The propensity of a liquid sample to load correctly, without being pinned, into a small reservoir or well (i.e., to "fill" the reservoir or well) is characterized by the Bond number ($B_o$) (also termed the Eötvös number). The Bond number can be calculated according to the following equation:

$$B_o = \frac{\rho g L^2}{\sigma}$$

where $\rho$ is the density of the sample, g is gravitational acceleration, L is a characteristic dimension of the reservoir/well (e.g., the radius of the well at corner 84), and $\sigma$ is the surface tension at the sample-air interface. The Bond number represents a ratio of gravitational forces to surface tension forces. With a Bond number of greater than one, gravity dominates surface tension, and below one, the converse holds. Filling wells with liquid sample becomes more reliable as the Bond number increases. Wells with very small Bond numbers (<0.01) generally fill only rarely without assistance, and wells with Bond numbers in the range between 0.01 and 1 can appear to behave stochastically in their filling properties. Filling may be encouraged with application of pressure or via a wicking force (derived from the contact angle), among others. In any event, the Bond number instructs a user as to whether or not wicking may need to be promoted to achieve proper filling. The well/sample combinations of the present disclosure may be characterized by a Bond number of less than about 1, 0.5, 0.2, or 0.1, among others.

Sample holder 60 may be composed of an upper member 102 and a lower member 104. The lower member may be attached to an underside or bottom surface of the upper member.

The upper member may be formed by injection molding a polymer (e.g., a thermoplastic or thermoset polymer, among others). The upper member, which interchangeably may be described as a perforated member, may define one or more through-holes each extending from the top side to the bottom side of the upper member and each providing side wall 66 of a well. The upper member also may define at least one groove 106 in a bottom surface of the upper member. The groove may form a ceiling and side walls of one or more channels (such as channel 70) that extend parallel to a plane defined by the upper member, the lower member, and/or an interface (e.g., a planar interface) between the upper member and the lower member. In other cases, the upper member may provide only a ceiling of one or more channels formed collectively with the lower member, or the side walls of one or more channels may be formed collectively by the upper and lower members.

The lower member may have any suitable structure. The lower member may be a polymer sheet, which may or may not be molded. The sheet may be substantially flat, with substantially planar top and bottom surfaces, which respectively may define one or more protrusions and/or dimples (see below). The sheet may be substantially thinner than the upper member, such as at least about 5-, 10-, or 20-fold thinner, among others, as measured parallel to central vertical axis 88. In some embodiments, the sheet may be a film having a thickness of less than about 2, 1, or 0.5 millimeters, among others. In exemplary embodiments, the upper member, the lower member, or both are formed of the different polymers or the same polymer, such as both being formed of a cyclic olefin copolymer (COO).

Further aspects of the upper and lower members, and exemplary features thereof, are described in Sections II-V.

Figure 3:
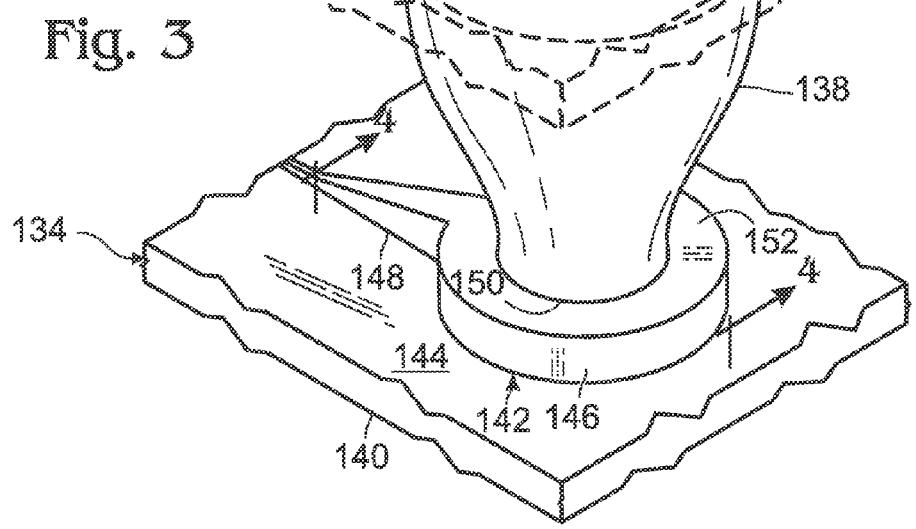
FIG. 3 is a fragmentary isometric view of a mold for producing the well of FIG. 1 by injection molding, in accordance with aspects of the present disclosure.
Figure 4:
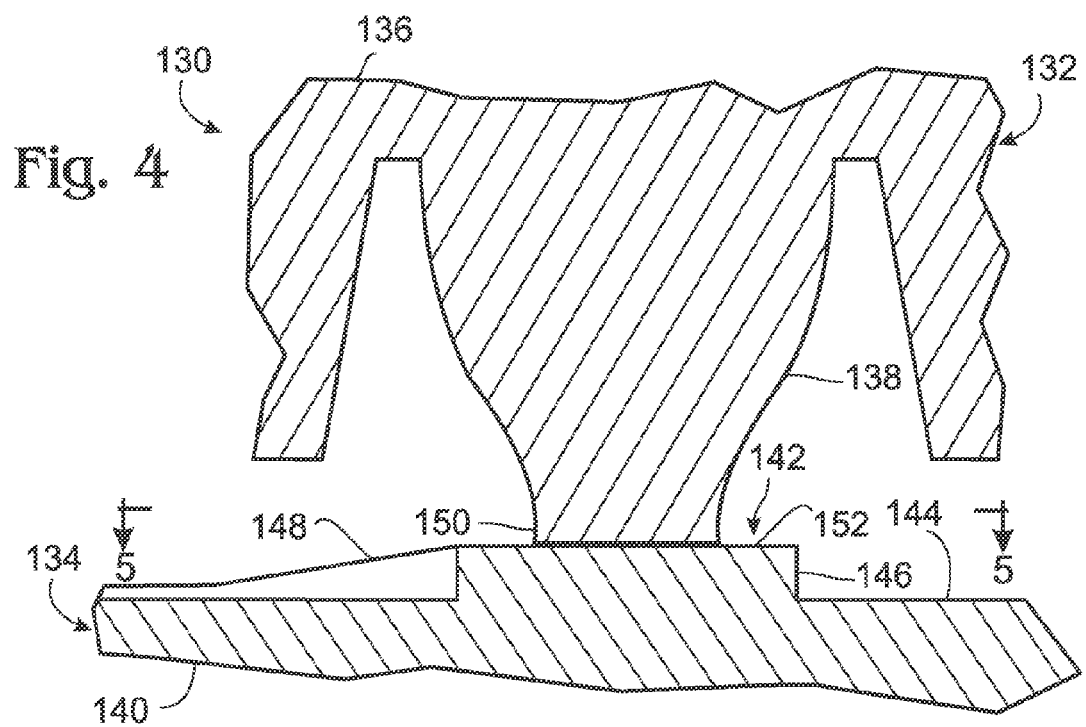
FIG. 4 is a sectional view of the mold of FIG. 3, taken generally along line 4-4 of FIG. 3.
Figure 5:
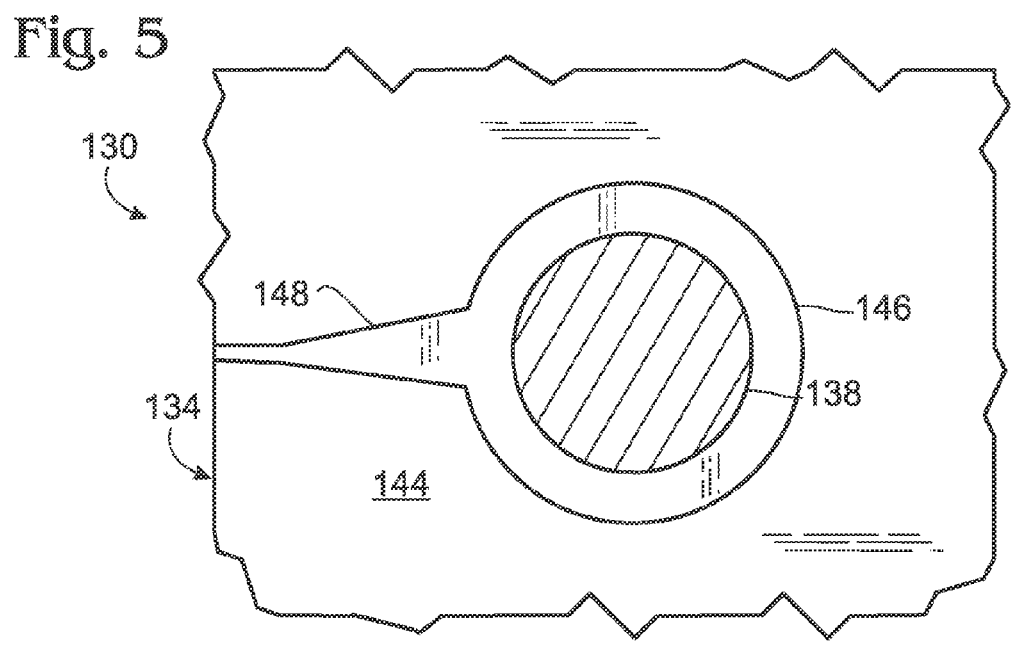
FIG. 5 is a sectional view of the mold of FIG. 4, taken generally along line 5-5 of FIG. 4.

FIGS. 3-5 shows part of a mold 130 for producing upper member 102 of sample holder 60 (FIG. 1) by injection molding. The structure of the mold generates corner 84 and overhang 90 (see FIG. 2). Mold 130 may be composed of a pair of engaged die members 132, 134 that collectively enclose a cavity defining the shape of upper member 102 of the sample holder.

First die member 132 may include a body 136 and a projection 138 (which may be described as a pin or core pin). The pin projects toward second die member 134 from body 136 in the assembled mold. Pin 138 fills the prospective upper region 92 of the well during the molding process and thus defines the shape and size of side wall 66 in the upper region. Pin 138 may have any suitable cross-sectional shape, such as circular, polygonal, oval, or the like. The pin may taper away from body 136.

Second die member 134 may include a base 140 and an elevated feature 142 projecting from a surface 144 of the base toward first die member 132. Elevated feature 142 may create a raised platform or pad 146 and a ridge 148 extending along surface 144 of the base from the pad. The pad and ridge respectively fill the prospective lower region 94 and channel 70 of the sample holder (see FIGS. 1 and 2) during the molding process. Accordingly, the pad and the ridge may determine the size and shape of lower region 94 and channel 70.

The pad may be engaged with a tip or distal end surface 150 of pin 138 in the assembled mold and thus may be described as a landing pad for pin 138. The pin may be engaged tightly with the pad to prevent flash from being formed between the pin and the pad when the upper member is injection molded. Pad 146 may be substantially cylindrical and/or disk-shaped (e.g., except for a draft angle). The pad may have a larger diameter than tip 150 of pin 138, such that a lateral margin 152 of the top of the pad is not engaged with tip 150.

In exemplary embodiments, intended for illustration only, the diameter of pad 146 may be about 2.5 mm and the diameter at the tip of pin 138 may about 2.3 mm, to provide a lateral margin 152 of about 0.1 mm. Also, the height (thickness) of pad 146 may be about 0.2 mm.

Second die member 134 may be formed by a body and at least one replaceable insert attached to the body. The insert may be formed of a softer material than the pin. High pressure used to tightly engage pin 138 with pad 146 may cause creep (gradual deformation) of the pad through repetitive utilization of the mold. Structuring the pad as oversized with respect to tip 150 may prolong the life of the insert by distributing the pressure exerted by pin 138 over a larger area of the pad, thereby reducing creep.

Pad 146 may determine the height and diameter of lower region 94 of the well (see FIG. 2). Corner 84 (see FIGS. 1 and 2) may be formed at the perimeter of the junction between pin 138 and pad 146.

II. Exemplary Wicking Promoters Formed as Floor Protrusions

This section describes exemplary floor protrusions formed by lower member 104 in a well of a sample holder to promote sample loading; see FIGS. 6-18. The sample holders described in this section may have any combination of features shown and/or described in Section I and/or elsewhere in the present disclosure.

Figure 6:
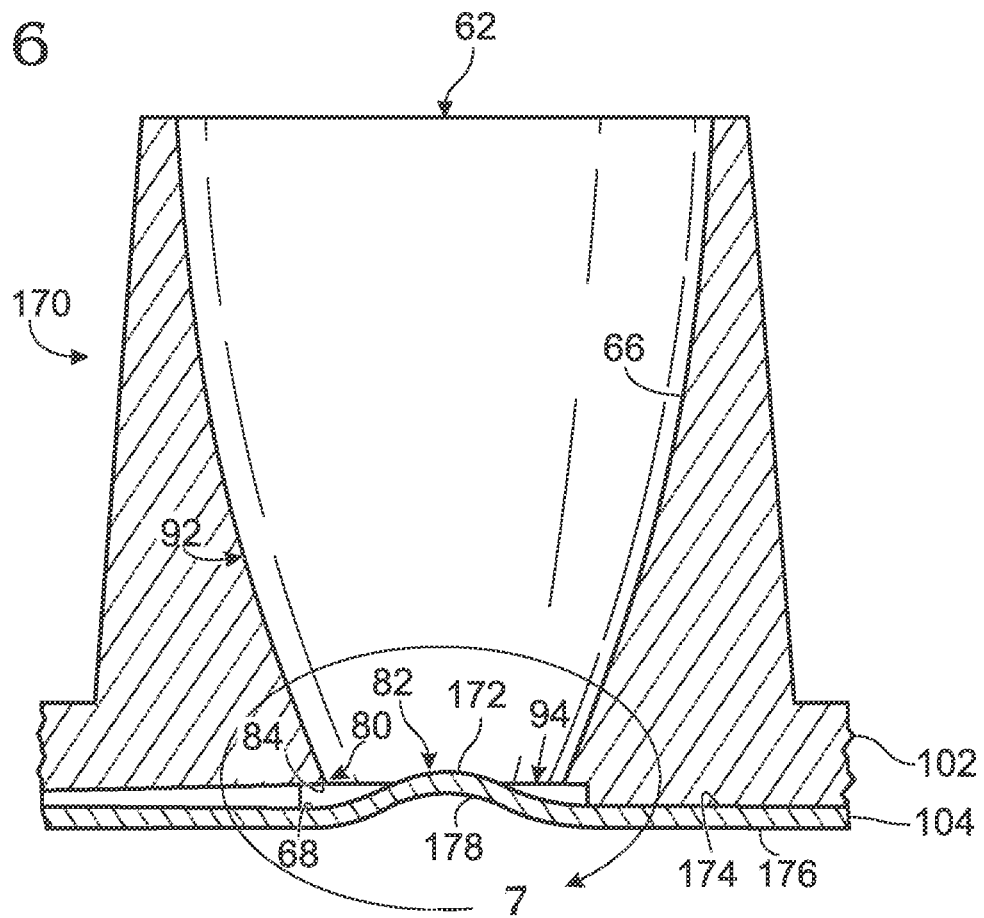
FIG. 6 is a fragmentary sectional view of an exemplary sample holder defining a well having a wicking impediment and also having a wicking promoter structured as a floor protrusion that encourages a sample to wet the well below the wicking impediment, in accordance with aspects of the present disclosure.

FIG. 6 shows a sample holder 170 having a wicking promoter 82 structured as a floor protrusion 172. The protrusion is formed by lower member 104, and is defined by a top surface 174 of the lower member. Protrusion 172 interchangeably may be described as a bulge, a projection, a bump, or the like. The protrusion may project upward from a planar surface region formed by top surface 174 around the protrusion. The protrusion may have a height above the planar surface region, of at least about 50, 100, or 200 micrometers, among others, and a height of less than about 1, 2, or 5 millimeters, among others.

The floor protrusion may project upward in well 62 to an elevation sufficient for contact with a dispensed sample. For example, the protrusion may project to an elevation that is at least about or higher than, the elevation of wicking impediment 80 (e.g., corner 84). In some cases, the protrusion may achieve contact with the sample even if the apex of the protrusion is positioned at an elevation lower than corner 84, such as when the sample forms a convex meniscus at interface 96 (e.g., see FIG. 1). In some embodiments, the protrusion may project through lower region 94 and at least about 25, 50, or 100 micrometers into upper region 92, and/or may project less than about 0.5, 1, or 2 millimeters into the upper region.

Protrusion 172 may have any suitable shape. The protrusion may be rounded, conical, spherical, polyhedral, or the like. Protrusion 172 may or may not include one or more ridges.

An opposing bottom surface 176 of the lower member may define a dimple 178 (interchangeably termed an indentation) under the protrusion. The dimple may be aligned with the protrusion, such as coaxial with the protrusion. Dimple 178 may be complementary to protrusion 172.

FIGS. 7-10 depict sample holder 170 at different stages of an exemplary filling progression for sample 64. Protrusion 172 prevents the sample from being pinned above the bottom of well 62 at corner 84 (e.g., see FIG. 1).

Figure 7:
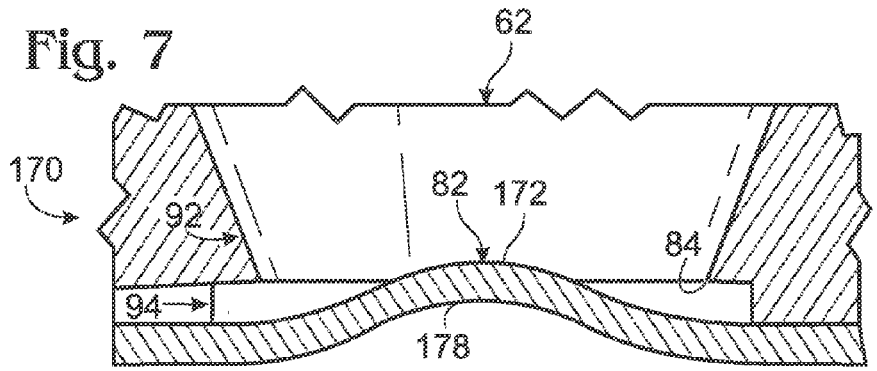
FIG. 7 is a magnified view of the sample holder of FIG. 6, taken generally at the region indicated at "7" in FIG. 6.
Figure 8:
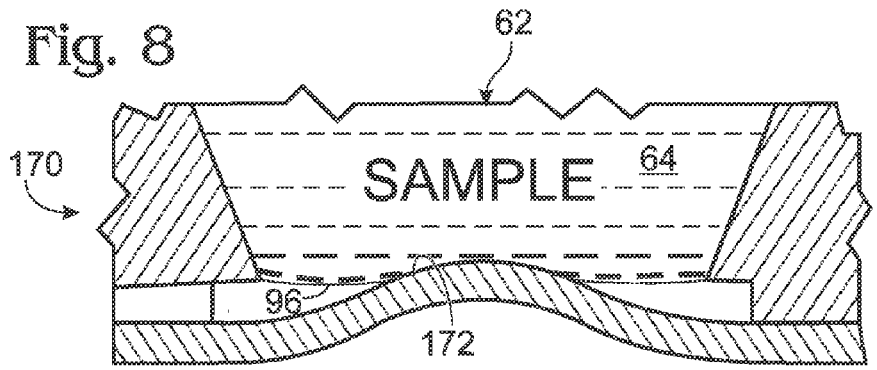
FIGS. 8-10 are magnified views of the sample holder of FIG. 6, taken generally as in FIG. 7 at different stages of a sample filling progression that illustrates how the floor protrusion may encourage a sample to load into a lower region of the well below the wicking impediment, in accordance with aspects of the present disclosure.

FIGS. 7 and 8 show well 62 respectively before and after sample 64 has been dispensed into the well. In FIG. 8, sample 64 is in contact with protrusion 172 and sample interface 96 forms a ring around the protrusion. In other cases, the sample may contact the protrusion asymmetrically at this stage of the filling progression (e.g., contacting the protrusion on only one lateral side). In any event, in the absence of protrusion 172, the filling progression may be stalled at this point, with the sample pinned in the well.

Figure 9:
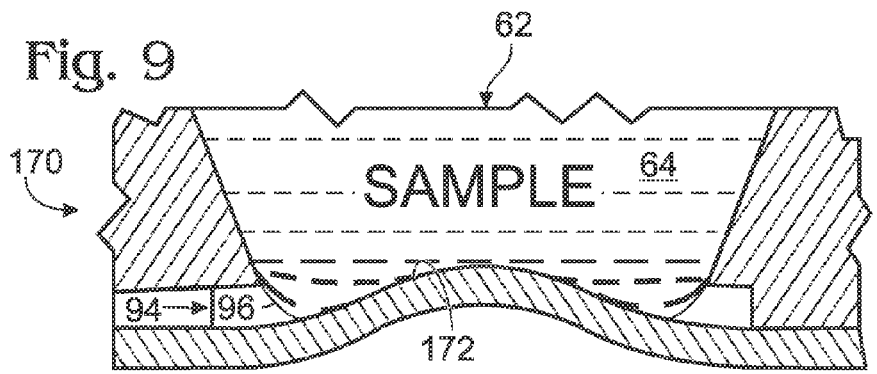

FIG. 9 shows sample 64 in the process of filling lower region 94 of the well. The sample has wicked to near the base of protrusion 172 and is spreading radially outward on the floor of the well. However, the corner may continue to block wicking at the perimeter of lower interface 96.

Figure 10:
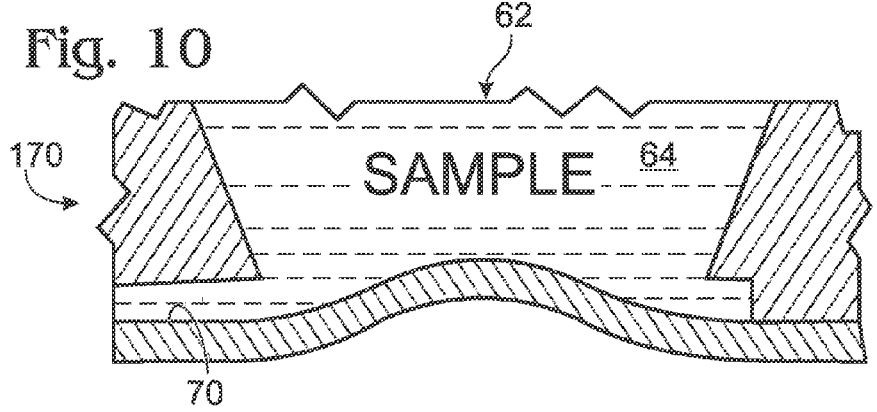

FIG. 10 shows well 62, and particularly the lower region thereof, filled with sample 64. The sample has wicked past the wicking impediment and into channel 70. In some cases, one or more air bubbles still may be trapped in the lower region of the well after the well has been correctly loaded and sample 64 has entered channel 70.

Figure 11:
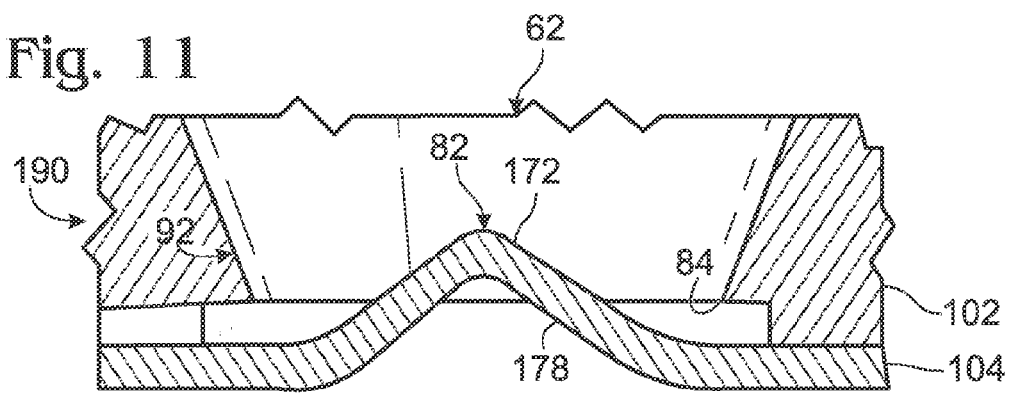
FIG. 11 is a fragmentary sectional view of another exemplary sample holder defining a well having a floor protrusion structured as a wicking promoter, with the view taken generally as in FIG. 7, in accordance with aspects of the present disclosure.
Figure 12:
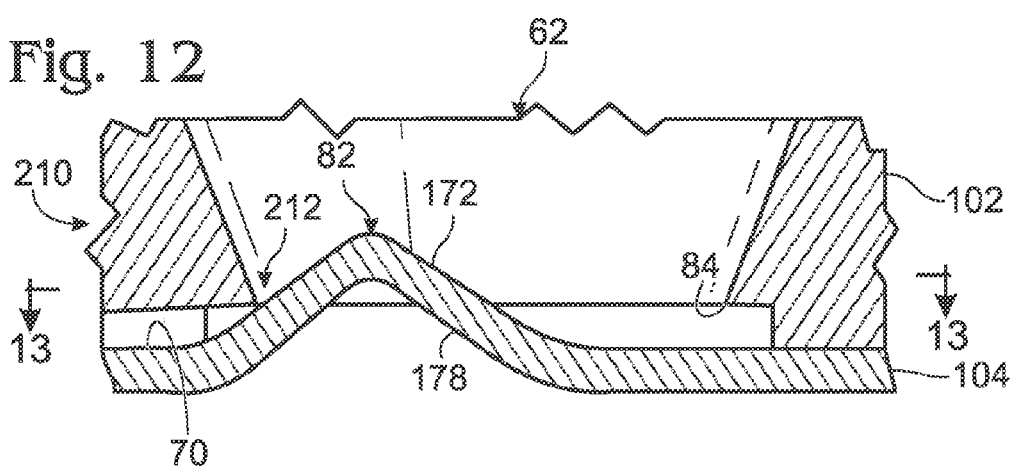
FIG. 12 is a fragmentary sectional view of an exemplary sample holder defining a well having an off-center version of the floor protrusion of FIG. 11, in accordance with aspects of the present disclosure.
Figure 13:
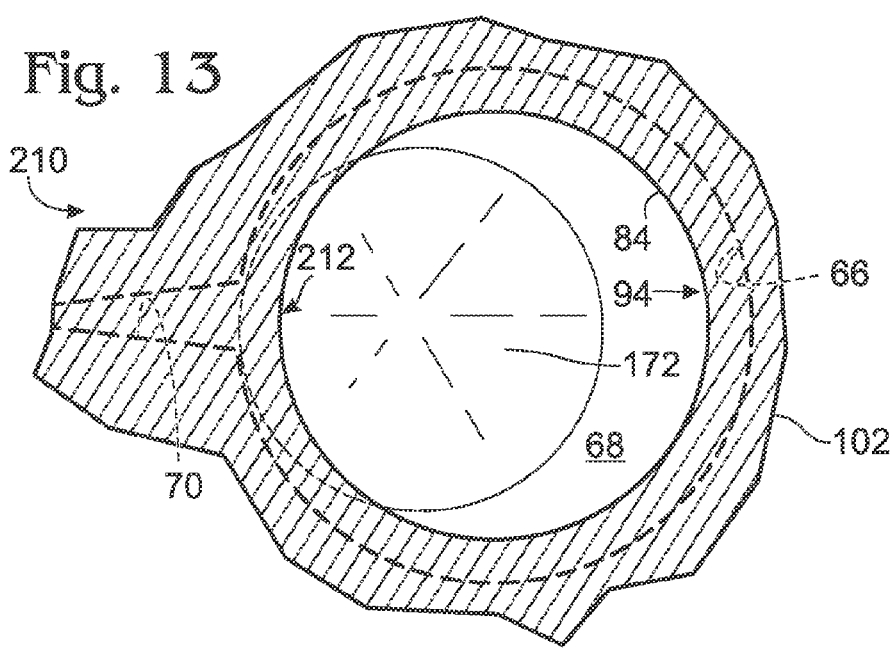
FIG. 13 is a fragmentary sectional view of the sample holder of FIG. 12, taken generally along line 13-13 of FIG. 12.

FIGS. 11-13 show exemplary sample holders 190, 210 having a conical floor protrusion 172. The protrusion projects above corner 84 into frustoconical upper region 92 of well 62. In sample holder 190, the protrusion is centered in the well, with the protrusion arranged coaxial to the central vertical axis of the well. In sample holder 210, the protrusion is positioned off-center and may contact corner 84, indicated by an arrow at 212. Positioning protrusion 172 closer to channel 70 may permit the protrusion to act as a barrier that restricts the unwanted migration of any residual, trapped air bubbles from the lower region of the well into the channel. Accordingly, the shape and/or position of the protrusion may be configured to control the formation, location, and/or size of any air bubble(s) remaining at the bottom of the well. The protrusion thus may enable the well to retain less residual sample when the well is emptied, thereby increasing the efficiency of processing the sample.

FIG. 14 shows an exemplary sample holder 230 having a ribbed, cross-shaped floor protrusion 172 formed in the bottom of a well. More generally, the protrusion may have one ridge or a plurality of ridges (interchangeably termed ribs) that intersect one another. The ridges may be arranged radially. Areas 232 flanked by a pair of ridges and positioned remotely from the inlet of channel 70 may form pockets that help create and/or trap residual air bubbles.

FIGS. 15 and 16 show an exemplary sample holder 250 having a furcated or pocketed floor protrusion 172 formed in the bottom of a well. The floor protrusion may be generally U-shaped (e.g., having a half-moon shape) to form a convex side 252 and a concave side 254. The concave side may create a pocket. The protrusion may be oriented with the convex side proximal and the concave side distal to the inlet of channel 70. FIG. 16 shows how the concave side of the protrusion may trap an air bubble 256 in the pocket, to increase sample processing efficiency and/or to prevent the delayed entry of air into the channel.

FIG. 17 shows an exemplary sample holder 270 having a floor protrusion 172 formed without an opposing dimple defined by bottom surface 176 of lower member 104 (e.g., compare with FIG. 7). Lower member 104 may, for example, be molded to include protrusion 172. Accordingly, top surface 174 of the lower member may be formed monolithically to provide protrusion 172 and planar surface regions that surround the protrusion and abut upper member 102.

FIG. 18 shows another exemplary sample holder 290 having floor protrusion 172 formed without an opposing dimple defined by bottom surface 176 of lower member 104 (e.g., compare with FIG. 7). Here, floor protrusion 172 is formed as a mass 292 (interchangeably termed a protrusion member) attached to or deposited on a sheet member 294 of lower member 104.

III. Exemplary Construction of a Sample Holder with a Floor Protrusion

This section describes exemplary methods of constructing a sample holder having a floor protrusion; see FIG. 19. The method steps disclosed in this section and elsewhere in the present disclosure may be performed in any suitable order and combination, and may be modified as needed to form any of the sample holders disclosed herein.

FIG. 19 shows a flow diagram illustrating selected aspects of a method of constructing sample holder 190 having floor protrusions 172 (see FIG. 11). Sample holder 190 may be generated by (a) attaching upper member 102 to lower member 104 and (b) deforming the lower member to generate protrusions 172. In the present illustration, attachment and deformation are performed at about the same time with the aid of a tool 270, which may be described as a stamping tool.

Tool 270 may have a working face 272 configured to be pressed against bottom surface 176 of lower member 104. The face may be contoured to define projections 274 that protrude from a surrounding planar region 276 of face 272. Each projection 274 may correspond to a dimple 174 (and overlying protrusion 172) to be formed in the lower member.

Upper member 102 may be fabricated by injection molding (e.g., see FIGS. 3-5). The upper member may define one or more through-holes 280 bounded by side wall 66. Each through-hole represents a prospective well 62.

Lower member 104 may be a sheet of material, such as a film, which may be substantially featureless. The lower member may be placed against the upper member, with a top surface 174 of the lower member abutted with an underside or bottom surface 282 of the top member. Attachment may be promoted by application of heat, a solvent, an adhesive material, electromagnetic radiation, pressure, or any combination thereof, among others.

Tool 270 may be used to apply pressure and/or heat, among others, to the lower member 104, to promote attachment of the lower member to the upper member and to deform the lower member to generate protrusions 172.

In other embodiments, lower member 104 may be deformed to form protrusions 172 before or after the lower member is attached to upper member 102. Furthermore, the protrusions of the sample holder may be formed in parallel by the same tool, as shown here, or may be formed serially. In further embodiments, an upper member having a pre-formed side wall protrusion (e.g., see Section IV) may be attached to the lower member as generally described above, optionally obviating a need for the lower member to be deformed and/or define a floor protrusion.

IV. Exemplary Wicking Promoters Formed as Side Wall Protrusions

This section describes exemplary side wall protrusions formed by upper member 102 in a well of a sample holder to promote sample loading into the bottom of the well below a wicking impediment; see FIGS. 20-35. The sample holders described in this section may have any combination of features shown and/or described in Section I and/or elsewhere in the present disclosure.

FIGS. 20-23 shows an exemplary sample holder 310 having a side wall protrusion 312 configured as a wicking promoter 82. Protrusion 312 may be contiguous with corner 84, which acts as a wicking impediment, and may interrupt corner 84 where the protrusion projects inward, at least generally toward a central vertical axis of the well. The protrusion may be positioned at least substantially exclusively or completely in lower region 94 of the well, that is, below corner 84. Generally, the top of the protrusion may have the same elevation as corner 84. Protrusion 312 may (or may not) abut floor 68 (i.e., a top surface region of lower member 104). In any event, the side wall protrusion may project into the well from undercut portion 95 of the well (FIG. 23; also see FIG. 2). The protrusion may project out of undercut portion 95 to a position closer to the central vertical axis of the well than the closest approach of corner 84 to the central axis.

FIG. 23 shows a magnified view of sample holder 310 to illustrate an exemplary wicking pathway 314 for fluid travel to the bottom of the well. Fluid may flow past the wicking impediment created at corner 84 by wicking through a junction 316 (e.g., a concave corner) created where corner 84 meets side wall protrusion 312.

Figure 24:
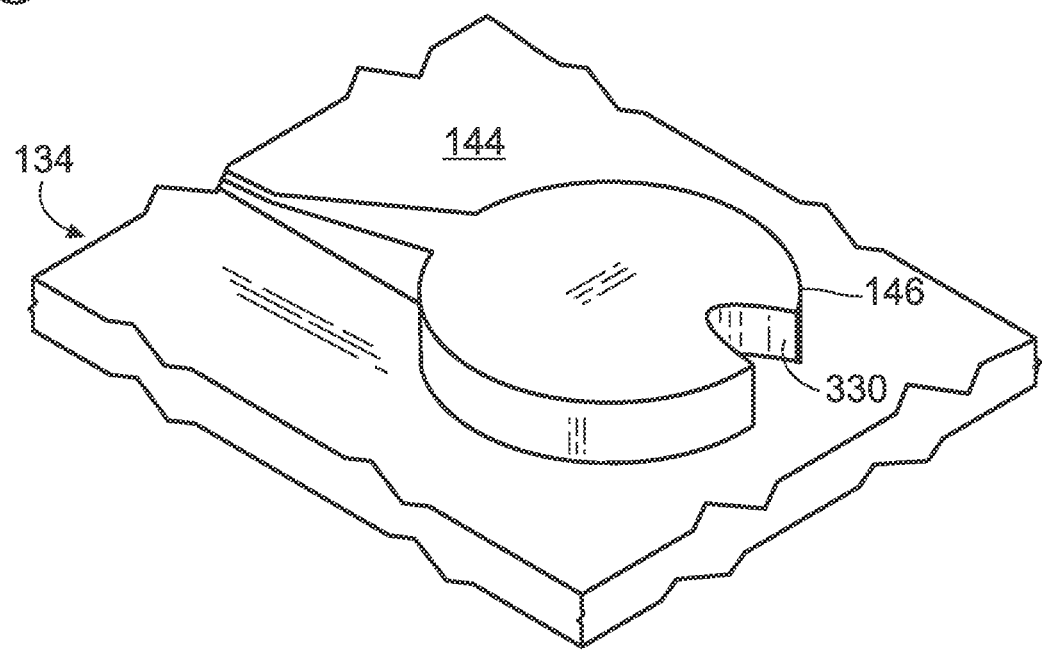
FIG. 24 is a fragmentary isometric view of an exemplary die member for a mold to produce an upper member of the sample holder of FIGS. 20-23, in accordance with aspects the present disclosure.
Figure 25:
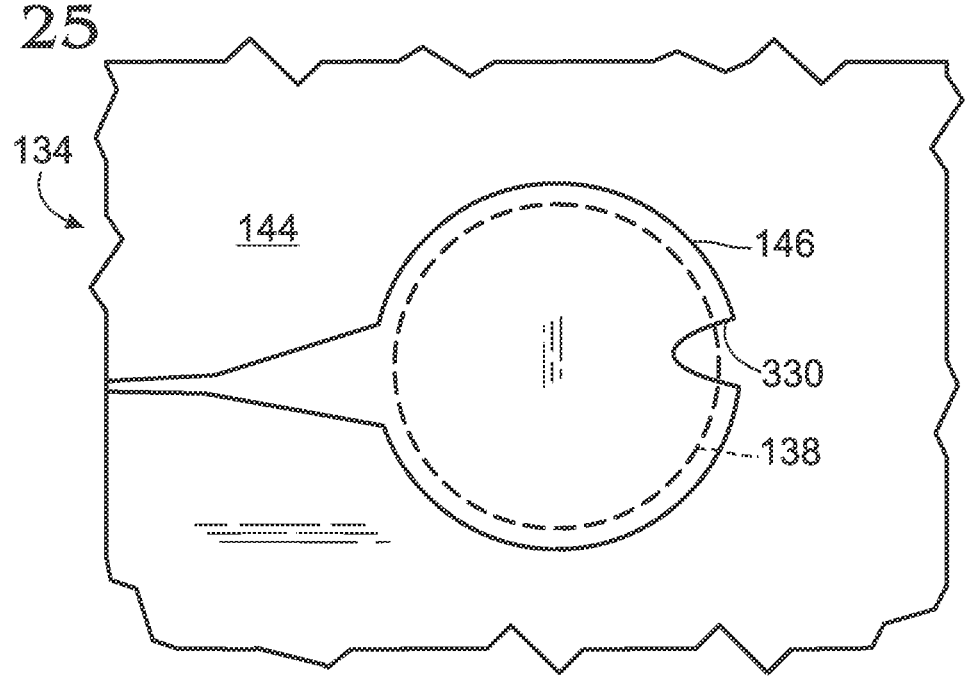
FIG. 25 is a fragmentary plan view of the die member of FIG. 24.

FIGS. 24 and 25 show an exemplary die member 134 for a mold (e.g., see FIGS. 3-5) to produce upper member 102 of sample holder 310 (see FIGS. 20-23). Pad 146 may define a notch 330 that is complementary to side wall protrusion 312. The notch may be open at the top and bounded at the bottom by base surface 144 of die member 134. Notch 330 may extend radially inward to a position closer to the central axis of pad 146 than the adjacent perimeter of pin 138 (shown dashed in FIG. 25).

Figure 26:
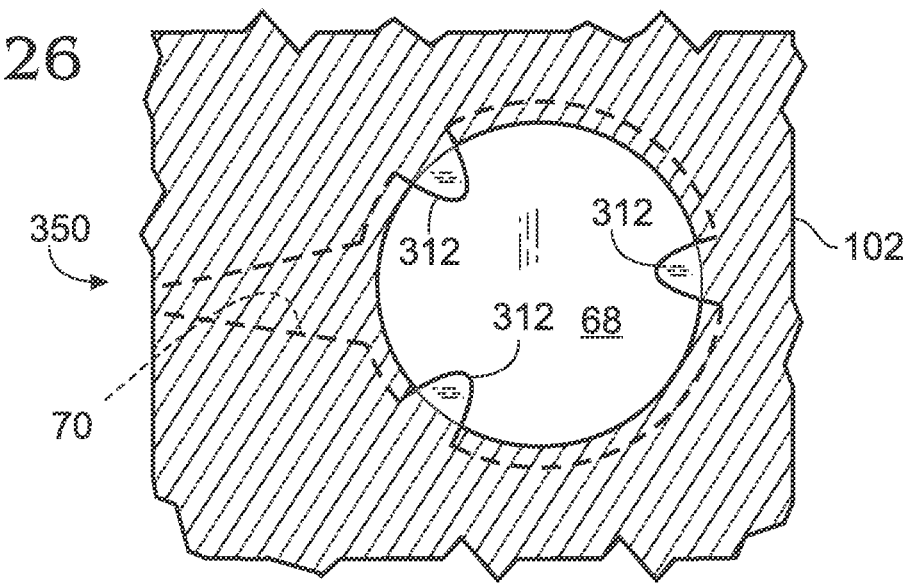
FIG. 26 is a fragmentary sectional view of an exemplary sample holder taken generally as in FIG. 20 and defining a well having a plurality of side wall protrusions that act as wicking promoters, in accordance with aspects of the present disclosure.

FIG. 26 shows an exemplary sample holder 350 viewed generally as in FIG. 20 and structured similarly to sample holder 310 except for having a plurality of the side wall protrusions 312 of holder 310. The protrusions may be arranged at spaced positions around the perimeter of the undercut region of the well.

Figure 27:
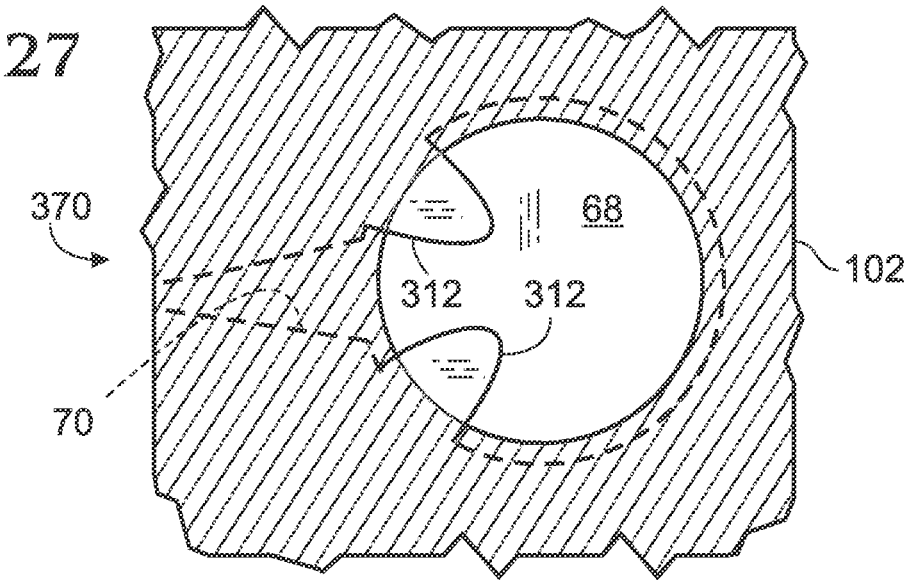
FIG. 27 is a fragmentary sectional view of yet another exemplary sample holder taken generally as in FIG. 20 and defining a well having a plurality of side wall protrusions that act as wicking promoters, in accordance with aspects of the present disclosure.

FIG. 27 shows yet another exemplary sample holder 370 viewed generally as in FIG. 20 and having a plurality of side wall protrusions 312 that act as wicking promoters. In sample holder 370, the side wall protrusions are larger than those of sample holder 350 (e.g., wider and projecting farther inward toward the center of the well). Also, the side wall protrusions may be positioned to opposingly flank the inlet to channel 70, which may facilitate creating and/or retaining a residual air bubble at the bottom of the well after the well is substantially emptied of sample.

Figure 28:
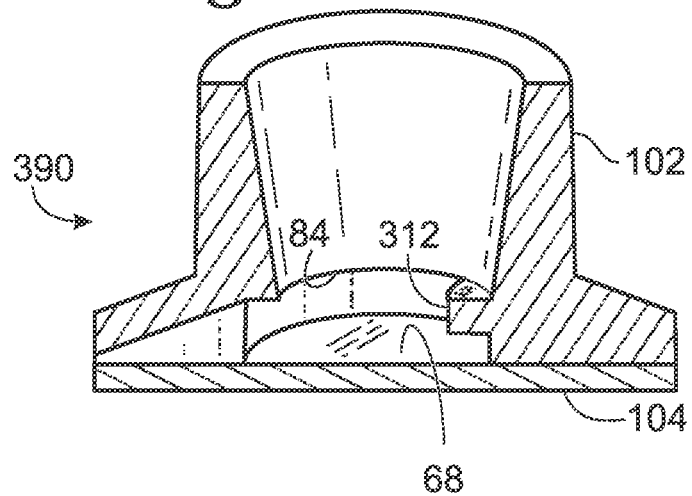
FIG. 28 is a fragmentary sectional view of an exemplary sample holder taken generally as in FIG. 21 and defining a well having a side wall protrusion that acts as a wicking promoter and is spaced from the floor of the well, in accordance with aspects of the present disclosure.

FIG. 28 shows an exemplary sample holder 390 viewed generally as in FIG. 21 and having an elevated side wall protrusion 312 that acts as a wicking promoter. The side wall protrusion may be contiguous with corner 84 and spaced from floor 68 of the well.

Figure 29:
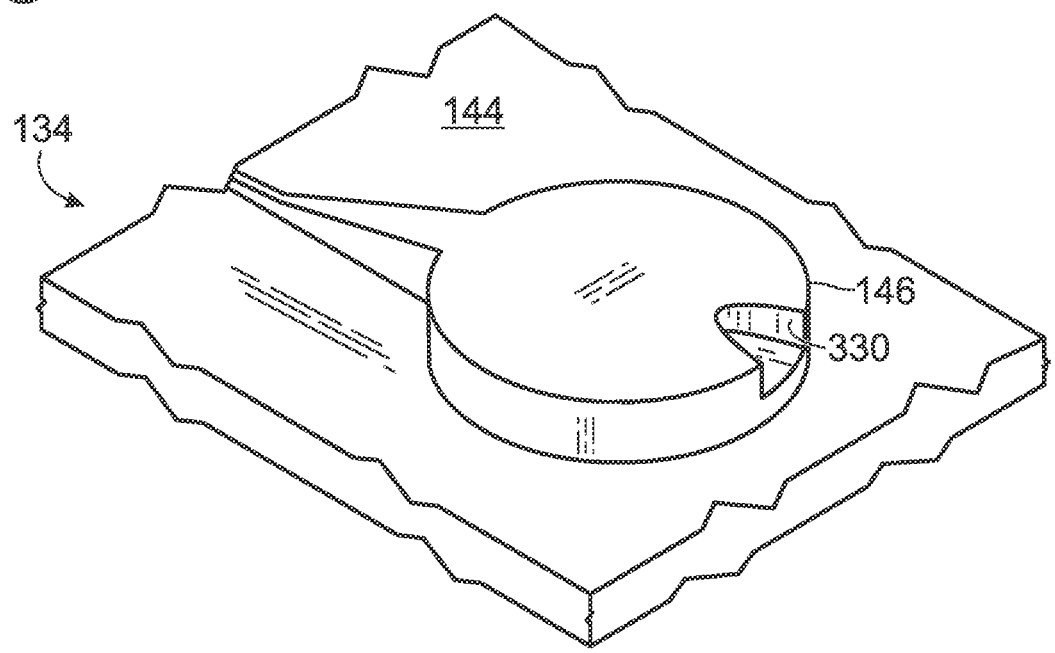
FIG. 29 is a fragmentary isometric view of an exemplary die member that may be used as part of a mold to form the well of FIG. 28, in accordance with aspects of the present disclosure.

FIG. 29 shows an exemplary die member 134 for a mold (e.g., see FIGS. 3-5) to produce upper member 104 of sample holder 390 (see FIG. 28). Pad 146 may define a notch 330 that is complementary to side wall protrusion 312 of holder 390. The notch may be open at the top and elevated at the bottom above base surface 144 of die member 134.

FIG. 30 shows an exemplary die member 134 for a mold (e.g., see FIGS. 3-5) to produce an upper member 104 having a side wall protrusion formed as a transverse ridge. The ridge is analogous to protrusion 312 of holder 310 (see FIGS. 20-23) except that the ridge may extend farther across the well, such as completely across lower region 94 to span the well transversely between spaced positions of side wall 66. Accordingly, pad 146 may define a slot 400 that extends across the pad to spaced perimeter sites of the pad and/or to at least generally opposing sides of the pad. The slot may be open at the top and bounded at the bottom by base surface 144 of die member 134. Alternatively, the slot may be elevated from surface 144, in a manner analogous to side wall protrusion 312 and notch 330 of FIGS. 28 and 29.

FIG. 31 shows an exemplary die member 134 for a mold (e.g., see FIGS. 3-5) to produce an upper member 102 having a side wall protrusion structured as plurality of ridges, which may or may not intersect one another. Branched slot 400 of pad 146 may be used to form the ridges, which are complementary to the slot.

FIGS. 32 and 33 show an exemplary mold 130 (also see FIGS. 3-5) for molding an upper member 102 of a sample holder. Pin 138 of first die member 132 may define a cavity 410 formed in a distal end surface 412 of the pin. The cavity may communicate with the perimeter of the distal end surface and may be complementary to a corresponding side wall protrusion in a well.

FIG. 34 shows an exemplary sample holder 430 formed using the mold of FIGS. 32 and 33. Holder 430 is equipped with an elevated, cantilevered side wall protrusion 432. The protrusion is structured as a finger with an enlarged end, disposed in upper region 92 of well 62, and formed at a junction with corner 84. Protrusion 432 may be positioned in contact with floor 68 of the well by deforming the protrusion through application of force, indicated by an arrow at 434. The protrusion may have a neck region and a head region. The head region may be generally spherical and disposed at an end of the neck region, with the head region spaced from the side wall of the well. The neck region may provide flexibility to the protrusion, allowing it to be bent towards floor 68.

FIG. 35 shows protrusion 432 after deformation, with the protrusion in contact with floor 68. The protrusion, and particularly the head region thereof, may or may not be attached to the floor of the well, such as by bonding, gluing, fusing, mechanical restraint, or the like. In any event, the protrusion may provide a wicking pathway having no substantial wicking impediment and extending from above corner 84 to floor 68, to encourage travel of sample to the bottom of the well.

V. Examples

This section describes selected aspects and embodiments of the present disclosure related to exemplary sample holders having wells configured to promote sample loading. These examples are intended for illustration only and should not limit or define the entire scope of the present disclosure.

Example 1

Exemplary Wicking with Beads

This example describes exemplary sample holders 450, 470 having a well 62 containing a wicking additive, namely, one or more beads 472 to promote flow of a sample past a wicking impediment to the bottom of the well; see FIGS. 36 and 37. The beads may be disposed in the well before or after sample has been dispensed into the well, or may be dispensed into the well along with the sample after being placed into contact with the sample.

FIG. 36 shows sample holder 450 having a single bead 472 disposed at the bottom of well 62. The bead may have a diameter that is at least about the height of corner 84 measured from the floor of the well. Accordingly, the top of the bead may be disposed above corner 84, as shown here. The bead may have a hydrophilic surface, namely, a surface that produces a contact angle with water of less than 90 degrees. The bead(s) may, for example, be formed of glass, a hydrophilic polymer, or the like. Bead 472 may or may not be attached to the floor of the well. In some embodiments, the bead may be sized to be pressed/snap-fitted into place for retention by the well. In some embodiments, the bead may be attached with glue, epoxy, or solvent bonding, among others.

FIG. 37 shows sample holder 470 having a plurality of beads 472 stacked at the bottom of well 62. The beads may function collectively as a wicking promoter, with the stack of beads having a height that is at least about the height of corner 84 measured from the floor of the well.

The beads shown in FIGS. 36 and 37 are spherical. However, beads with other shapes may be suitable.

In other embodiments, the bead(s) may be replaced with one or more fibers that are attached to the floor of the well and extend upward, such as above a plane defined by the wicking impediment. Each fiber may provide a wicking path for a sample.

Example 2

Exemplary Surface Modification to Promote Wicking

This example describes exemplary sample holders having a well with a modified surface to promote flow of a sample around a wicking impediment to the bottom of the well, and also describes methods of making the sample holders.

A sample holder, or a component thereof, may be treated with a surface modifying agent, to increase the hydrophilicity of a surface thereof. Exemplary surface modifying agents include a plasma (e.g., an oxygen plasma), an atomic vapor, ultraviolet radiation, or a fluid reactant that covalently modifies the surface, among others. The sample holder may be exposed to the agent before or after upper member 102 is attached to lower member 104.

Example 3

Exemplary Loading Features for an Upper Region of a Well

This example describes an exemplary sample holder having a well 62 with a well-filling aid or loading feature formed above a wicking impediment, to promote downward flow of fluid in the well; see FIGS. 38-43. In other embodiments, the loading feature may be incorporated into a well having a wicking impediment and a wicking promoter to overcome the wicking impediment, or a well having neither the impediment nor the promoter.

The reliability and robustness of properly loading a sample into a well may be dictated by two stages of filling. First, if the sample is introduced high in the well it may need to travel down the well into the bottom section. Second, the sample may need to travel past a wicking impediment formed where upper and lower regions of the well meet. This example describes well-filling aids for the first stage of filling, to enable sample to wick to the bottom section of the well quickly, reliably, and robustly.

Figure 38:
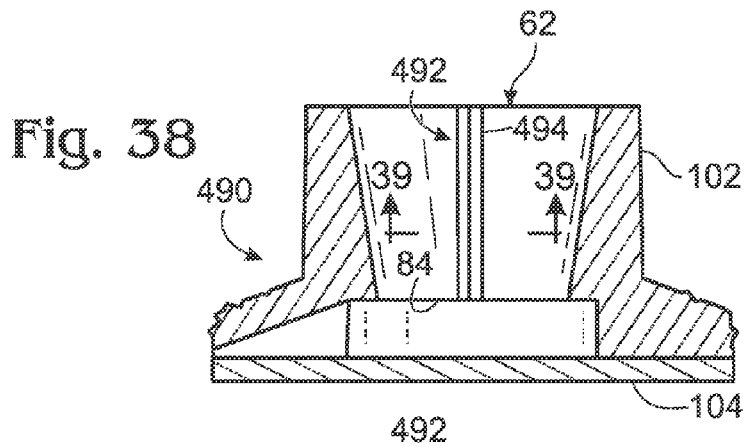
FIG. 38 is a fragmentary sectional view of an exemplary sample holder defining a well with a loading feature formed as ridge in an upper region of the well above a wicking impediment, in accordance with aspects of the present disclosure.
Figure 39:
FIG. 39 is a fragmentary sectional view of the sample holder of FIG. 38, taken generally along line 39-39 of FIG. 38 through the loading feature.
Figure 40:
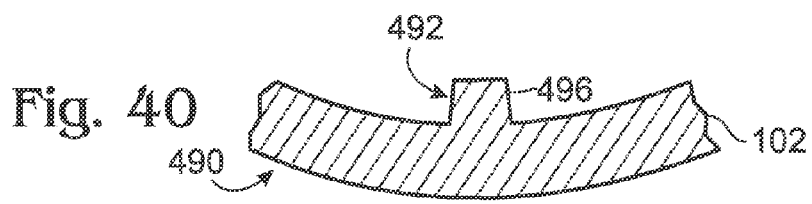
FIG. 40 is a fragmentary sectional view of another exemplary sample holder, with the view taken as in FIG. 39 through another exemplary embodiment of the loading feature of FIGS. 38 and 39, in accordance with aspects of the present disclosure.

FIGS. 38 and 39 show a sample holder 490 with a loading feature 492 formed by the side wall of the well and extending axially from the top of the well to corner 84. The loading feature may be a ridge 494 that projects inward from the well side wall. Here, the ridge has a triangular cross section, although other shapes may be suitable. For example, FIG. 40 shows another exemplary structure for loading feature 492, namely, a ridge 496 having a generally rectangular cross-section. As shown, the ridge may form at least one convex corner and at least one concave corner.

Figure 41:
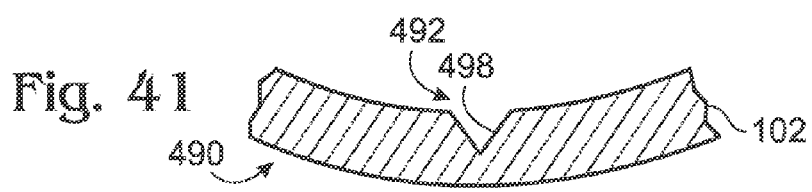
FIG. 41 is a fragmentary sectional view of yet another exemplary sample holder, with the view taken as in FIG. 39 through yet another exemplary embodiment of the loading feature of FIGS. 38 and 39, in accordance with aspects of the present disclosure.
Figure 42:
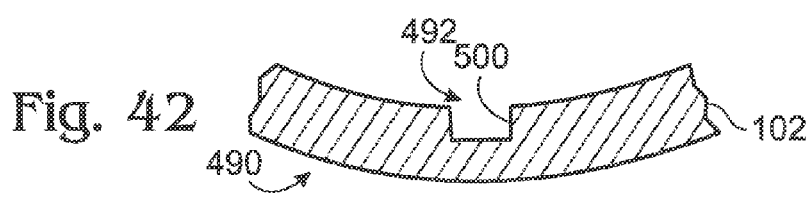
FIG. 42 is a fragmentary sectional view of still another exemplary sample holder, with the view taken as in FIG. 39 through still another exemplary embodiment of the loading feature of FIGS. 38 and 39, in accordance with aspects of the present disclosure.

FIGS. 41 and 42 show sample holder 490 with loading feature 492 formed by a groove 498 or 500 in the side wall of the well. The groove may be triangular, generally rectangular, or the like. The sample holder may have one or more loading features 492, which may be any combination of ridges and/or grooves. The loading features may be suitable for a well having a circular cross-section, such as a well with an at least generally frustoconical upper region 94.

Figure 43:
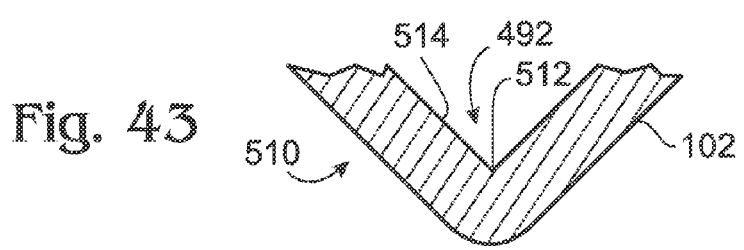
FIG. 43 is a fragmentary sectional view of still yet another exemplary sample holder, with the view taken as in FIG. 39 through still yet another exemplary embodiment of the loading feature of FIGS. 38 and 39, in accordance with aspects of the present disclosure.

FIG. 43 shows an exemplary sample holder 510 having a loading feature 492 formed as an axial, concave corner 512 in a well having a polygonal cross-sectional shape. The well may have a side wall 514 that abruptly changes in orientation as the wall extends around the central vertical axis of the well to form a plurality of concave corners. For example, in the depicted embodiment, side wall 514 forms a four-sided well having four wall portions that meet pairwise to generate corners 512.

Example 4

Exemplary Wicking Promotion with a Sample Loader

A sample loader may have a wicking promoter feature. For example, a pipet tip may contact the well bottom as sample is loaded, if the diameter of the pipet tip is sufficiently small to penetrate the narrowest part of the well. Alternatively, the pipet tip could have a small-diameter feature that extends to the well bottom and acts as a wicking promoter.

Example 5

Exemplary Sample Holder for Emulsion Production

This example describes an exemplary sample holder or chip 540 for emulsion production and including a floor protrusion in sample wells to promote sample loading; see FIGS. 44-49. The floor protrusion shown in this example may be replaced and/or augmented by any of the wicking promoters and/or loading features disclosed herein.

The term "chip" in the present disclosure describes any device for holding and manipulating fluids, such as prospective and actual emulsion phases. The device may not (or may) include electrical and/or electronic structure. The terms "microfluidic chip" and "microfluidic device" are interchangeable. The term "microfluidic" means that the chip/device defines at least one channel with a characteristic dimension (e.g., diameter, width, and/or depth) of less than one millimeter. A microfluidic chip is not limited otherwise in size, shape, or functionality, except when expressly specified.

Figure 44:
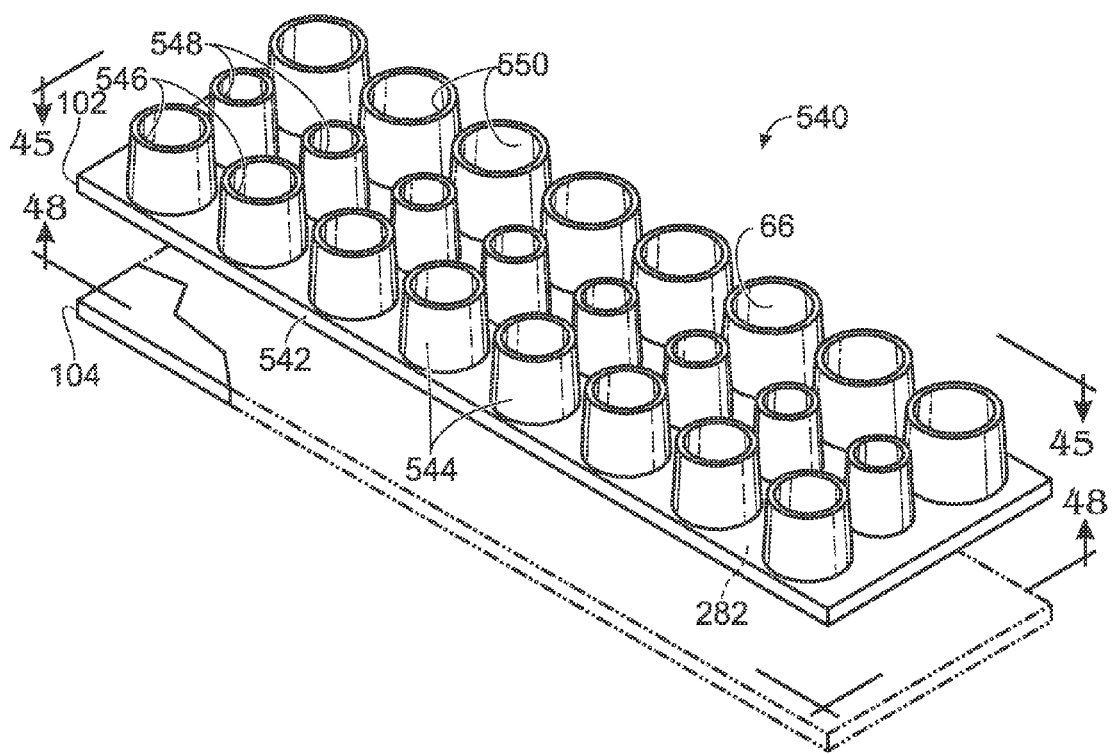
FIG. 44 is an exploded view of an exemplary sample holder having a plurality of emulsion formation units each having a plurality of wells and being equipped with at least one wicking promoter in at least one of the wells, in accordance with aspects of the present disclosure.

FIG. 44 shows an exploded view of sample holder 540. The sample holder may be used for emulsion formation only once (i.e., a disposable chip) or may be used more than once (i.e., a reusable chip). The sample holder may be composed of upper member 102 and lower member 104. The upper and lower members may be substantially irreversibly attached to each other, such as by bonding and/or with an adhesive, among other words. In other words, the sample holder (and/or upper member 102 and/or lower member 104) may have a unitary (one-piece) structure, meaning that the holder (and/or member 102/104) cannot be separated into two or more pieces without damaging the holder/member, such as by cutting, breaking, tearing, melting, dissolving, etc. Upper member 102 may form a bottom region or base 542 and a plurality of tubular projections 544 projecting upward from the base. Each tubular projection may form at least an upper part of side wall 66 of one of wells 546-550. Lower member 104, which may or may not be a substantially featureless sheet of material or film, may seal a bottom surface 282 of upper member 102 (also see FIG. 19).

Figure 45:
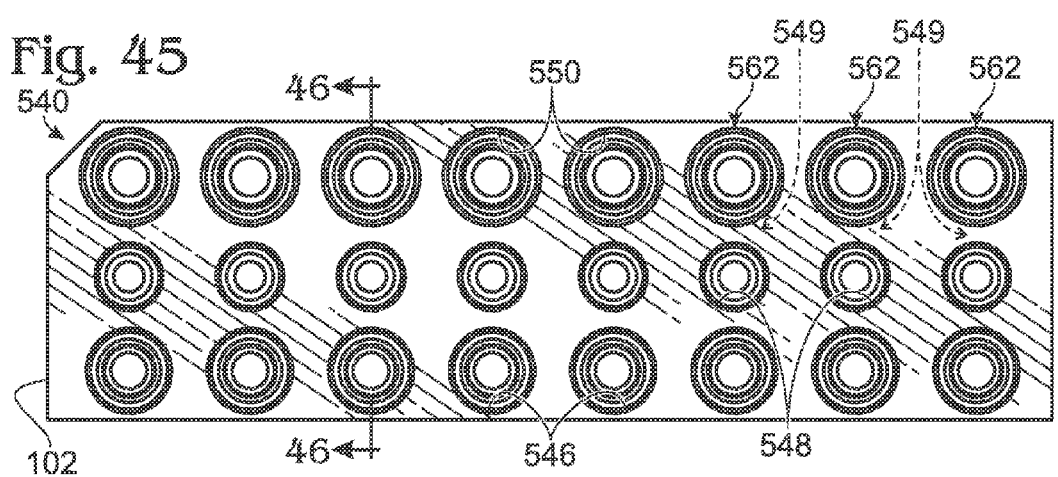
FIG. 45 is a plan view of the sample holder of FIG. 44, taken generally along line 45-45 of FIG. 44.
Figure 46:
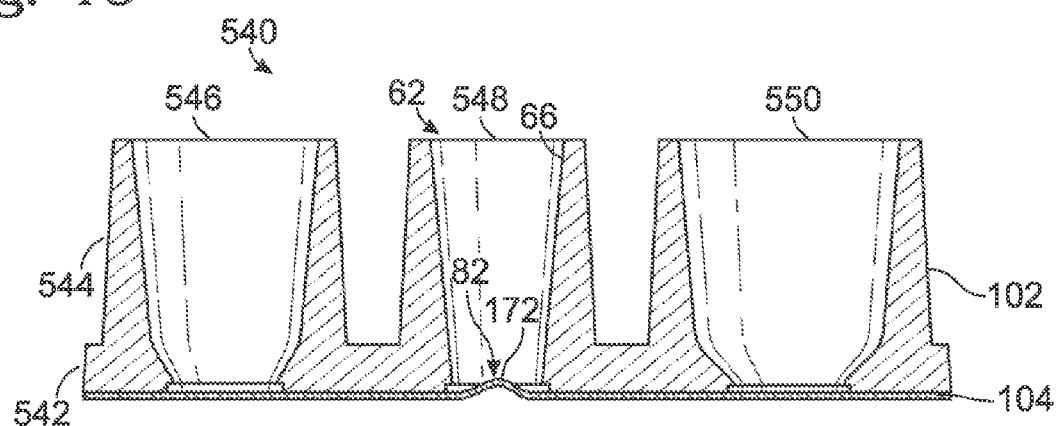
FIG. 46 is a sectional view of the sample holder of FIG. 44, taken generally along line 46-46 of FIG. 45.

FIGS. 45 and 46 show respective plan and sectional views of holder 540. The holder may provide a plurality of wells for holding emulsion phases. A subset of the wells, such as input wells 546, 548 (also termed inlet wells), may provide input reservoirs to receive and hold prospective emulsion phases, and to supply the continuous phase to one or more droplet generators 549 of the chip. Another subset of the wells, such as output wells 550 (also termed outlet wells), may provide output containers to receive and collect one or more emulsions from droplet generators 549.

Holder 540 may provide one or a plurality of emulsion formation units 562 each including a droplet generator 549. Units 562 may be substantial copies of one another. The emulsion formation units may be in fluid isolation from each other, such that there is no sharing or mixing of emulsion phases among the units, or may share an input reservoir (such as for a continuous phase). In any event, the units may be used to form a corresponding plurality of separate emulsions collected in the output containers (e.g., wells 550).

Wells 546-550 may have any suitable arrangement. The wells may be arranged in rows and columns. In some cases, each column (or row) may be part of a different emulsion formation unit 562. The wells may be spaced in correspondence with a standard well-to-well spacing of a microplate, as published by the American National Standards Institute (ANSI) on behalf of the Society for Biomolecular Screening. For example, the wells within each row may have a center-to-center spacing of about 18, 9, 4.5, 2.25, or 1.125 millimeters, among others. The wells of the same emulsion formation unit (e.g., the wells of a column) may or may not have a spacing that corresponds to a standard microplate well spacing.

Wells 546-550 may have any suitable size and shape. For example, each of the wells in a row may be substantial copies of one another, having the same size, shape, and volume. Wells of different rows and/or within the same column may have different sizes, shapes, and/or volumes. The wells may be configured to form a seal when juxtaposed with a suitably formed gasket. In particular, the top surface of each well may be substantially planar. The top surfaces of wells may be coplanar to enable forming a seal with a single substantially planar gasket. In the depicted embodiment, wells 550 are largest, wells 546 are intermediate in size, and wells 548 are smallest. The wells of a row and/or all of the wells may have the same height, to form a planar top surface of the holder.

Wells 548, among others, may include a wicking promoter 82, such as floor protrusion 172, among others.

Figure 47:
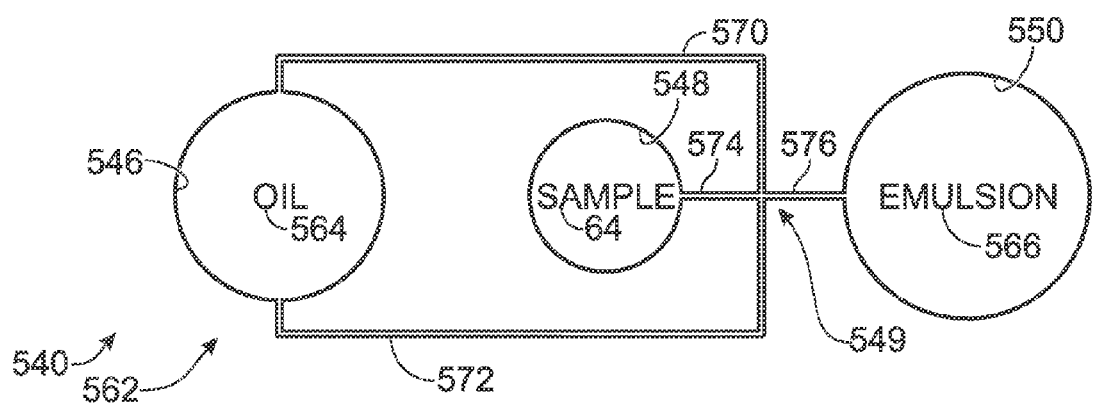
FIG. 47 is a somewhat schematic bottom view of a single emulsion formation unit of the sample holder of FIG. 44, in accordance with aspects of the present disclosure.

FIG. 47 shows a somewhat schematic bottom view of a single emulsion formation unit 562 of holder 540. Wells 546, 548 may hold and supply prospective emulsion phases, such as an oil phase 564 and an aqueous sample 64. Collection well 550) may receive and collect an emulsion 566 formed by droplet generator 549 from oil phase 564 and sample 64. Input wells 546, 548 and collection well 550 may be fluidically interconnected via channels 570-576 that intersect at droplet generator 549. The channels may include one or a pair of oil inlet channels 570, 572, a sample inlet channel 574, and an emulsion outlet channel 576. In some embodiments, each of oil inlet channels 570, 572 may extend from a different input well. In some embodiments, the emulsion formation unit may include only one oil inlet channel. Exemplary emulsion phases and other exemplary configurations for droplet generators, channels, input reservoirs, and collection containers, among others, that may be suitable for holder 540 are described in the patent documents listed above under Cross-References, which are incorporated herein by reference, particularly U.S. Patent Application Publication No. 2010/

0173394 A1, published Jul. 8, 2010; and U.S. patent application Ser. No. 13/287,120, filed Nov. 1, 2011.

Figure 48:
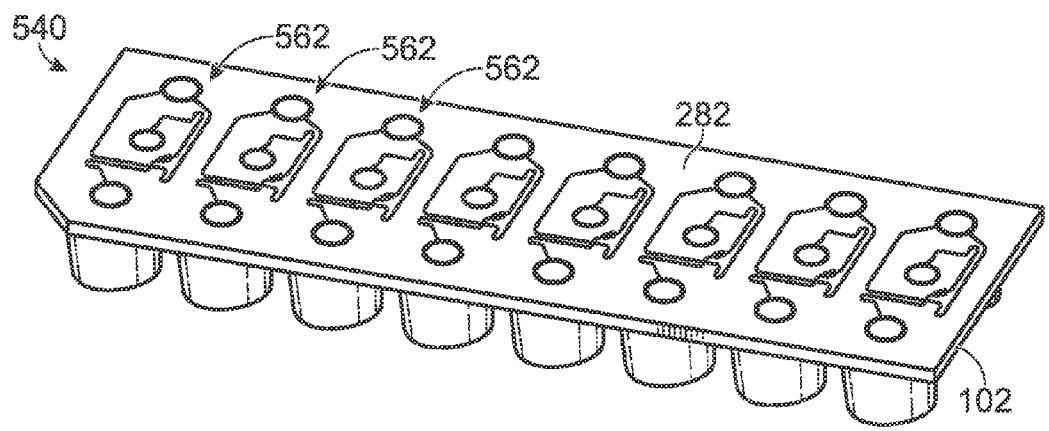
FIG. 48 is a bottom view of an upper member of the sample holder of FIG. 44, taken generally along line 48-48 of FIG. 44.
Figure 49:
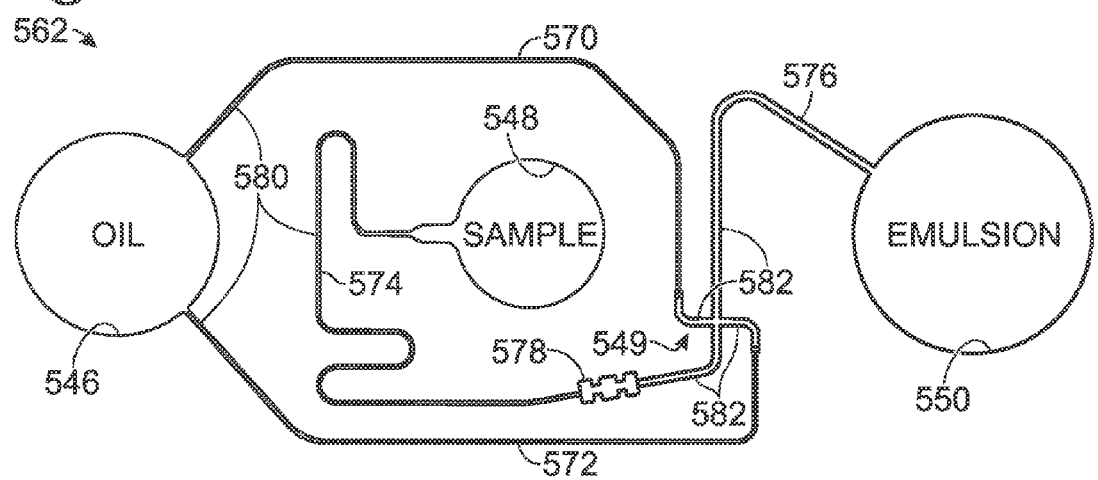
FIG. 49 is a less schematic bottom view of the single emulsion formation unit of FIG. 47.

FIGS. 48 and 49 show less schematic, bottom views of emulsion formation units 562 (FIG. 48) or one of the units (FIG. 49) of holder 540 in the absence of lower member 104. Channels 570-576 and droplet generator 549 of each unit 562 may be formed predominantly in bottom surface 282 of upper member 102, with only a floor of each channel and droplet generator formed by lower member 104. In other embodiments, at least a portion of one or more of the channels and/or the droplet generator of each unit 562 may be formed in the top surface of lower member 104.

Channels 570-576 may have different cross-sectional sizes (i.e., diameters/widths and/or depths) and/or lengths and/or may vary in size along each channel. The cross-sectional size(s) and the lengths may be selected to provide a desired resistance to flow and thus a desired ratio of emulsion phases flowing through droplet generator 549, to form droplets of the desired size, to enhance droplet stabilization after droplet formation, to form at least one air trap 578 in an inlet channel (e.g., sample inlet channel 574), or any combination thereof, among others.

In exemplary embodiments, channels 570-576 form a channel network that interconnects the wells of an emulsion formation unit. The channel network may have a narrower/shallower region 580 for greater flow resistance, and a wider/deeper region 582 downstream of region 580 for droplet formation and stabilization. In other words, the cross-sectional size of the channel network may increase toward the collection container of the unit. Region 582 may begin upstream of droplet generator 549 for each of the inlet channels and may extend from the droplet generator via outlet channel 576. Each channel may taper in a direction parallel to the depth axis of the channel. For example, each channel may taper toward the top (or the bottom) of the holder. In some cases, each channel may have a trapezoidal cross-sectional shape and/or may have a depth and a width that are about the same. In exemplary embodiments, intended only for illustration, channel portions of region 580 may have a depth and a width of about 50-100, or 60-80 micrometers, among others, channel portions of region 582 may have a width and a depth of about 80-150 or 90-120 micrometers, among others, and the droplets generated may have a volume of about 0.1-10 nanoliters, among others. Further aspects of channel shapes and sizes that may be suitable for the holder are described in the patent documents listed above under Cross-References, which are incorporated herein by reference.

Example 6

Selected Embodiments

This example presents selected embodiments of the present disclosure related to a sample holder defining a well having a wicking promoter and methods of making and using the sample holder. The selected embodiments are presented as a set of numbered paragraphs.

1. A device for holding a sample of small volume, comprising: a holder including an upper member attached to a lower member to form a well having a side wall and a floor, the side wall creating a wicking impediment conceptually dividing the well into an upper region and a lower region, the well including a wicking promoter adapted to encourage a sample to wick from the upper region to the lower region.

2. A device for holding a sample of small volume, comprising: a holder including an upper member attached to a lower member to form a well having a side wall and a floor, the side wall creating a convex corner that extends about a central vertical axis of the well to conceptually divide the well into an upper region and a lower region and capable of acting as an impediment to wicking of a sample from the upper region to the lower region, the well including a protrusion defined by the upper member, the lower member, or both the upper member and the lower member collectively, and adapted to promote wicking of the sample into the lower region from the upper region.

3. The device of paragraph 2, wherein the protrusion is a floor protrusion defined by the lower member.

4. The device of paragraph 3, wherein the lower member defines a dimple under the floor protrusion.

5. The device of paragraph 3 or 4, wherein the lower member is a sheet member having a top surface and a bottom surface, and wherein the sheet member is deformed such that the top surface defines the floor protrusion and the bottom surface defines the dimple.

6. The device of paragraph 3, wherein a bottom surface of the lower member under the floor protrusion is flat.

7. The device of paragraph 3 or 4, wherein the lower member includes a sheet member and a projecting member attached to a top surface of the sheet member and forming the floor protrusion.

8. The device of paragraph 7, wherein the projecting member is attached to the sheet member by solvent bonding, thermal bonding, glue bonding, ultrasonic bonding, a mechanical connection, or a combination thereof.

9. The device of any of paragraphs 3 to 8, wherein the floor protrusion is at least generally conical.

10. The device of any of paragraphs 3 to 9, wherein the protrusion has a rounded tip.

11. The device of any of paragraphs 3 to 10, wherein the protrusion forms at least one ridge.

12. The device of paragraph 11, wherein a crest of the at least one ridge projected onto a plane orthogonal to the central vertical axis of the well follows a nonlinear path.

13. The device of paragraph 11 or 12, wherein the ridge has a concave side and a convex side arranged laterally to each other.

14. The device of paragraph 13, wherein the well communicates with a channel inlet, and wherein the convex side is closer than the concave side to the channel inlet.

15. The device of any of paragraphs 11 to 14, wherein the at least one ridge includes a plurality of ridges.

16. The device of paragraph 15, wherein the plurality of ridges are arranged radially.

17. The device of any of paragraphs 2 to 16, wherein the protrusion projects from the lower region into the upper region of the well, and/or projects above a plane defined by the convex corner.

18. The device of paragraph 2, wherein the protrusion is a side wall protrusion defined by the upper member.

19. The device of paragraph 18, wherein a top of the side wall protrusion is disposed at a same elevation as the convex corner.

20. The device of paragraph 18 or 19, wherein the side wall protrusion abuts the lower member.

21. The device of paragraph 18 or 19, wherein the side wall protrusion is spaced from the lower member to form a gap between the protrusion and the lower member.

22. The device of any of paragraphs 18 to 21, wherein the side wall protrusion projects at least generally toward the central vertical axis from the side wall.

23. The device of any of paragraphs 18 to 22, wherein the side wall protrusion is disposed at a junction of the side wall and the floor.

24. The device of any of paragraphs 18 to 23, wherein a minimum distance of the side wall protrusion from the central vertical axis is less than a minimum distance of the convex corner from the central vertical axis.

25. The device of any of paragraphs 18 to 24, wherein the side wall protrusion is contiguous with the convex corner.

26. The device of any of paragraphs 18 to 25, wherein the side wall protrusion projects from the side wall at only a single site.

27. The device of any of paragraphs 18 to 26, further comprising one or more additional side wall protrusions disposed in the well and adapted to promote wicking of the sample into the lower region from the upper region.

28. The device of any of paragraphs 18 to 27, wherein the side wall protrusion includes a ridge that extends completely across the well.

29. The device of any of paragraphs 1 to 28, wherein the well has a minimum inner diameter of less than 10 millimeters.

30. The device of any of paragraphs 1 to 29, wherein the side wall is undercut adjacent the convex corner.

31. The device of any of paragraphs 1 to 30, wherein the lower member includes a film.

32. The device of any of paragraphs 1 to 31, wherein the well widens below the convex corner.

33. The device of any of paragraphs 1 to 32, wherein the upper region has a minimum diameter that is less than a diameter of the lower region.

34. The device of any of paragraphs 1 to 33, wherein the upper region tapers toward the convex corner.

35. The device of any of paragraphs 1 to 34, wherein the well is stepped.

36. The device of any of paragraphs 1 to 35, wherein the holder defines a channel that communicates with the lower region of the well.

37. The device of paragraph 36, wherein the channel tapers away from the lower region of the well.

38. The device of paragraph 36 or 37, wherein the holder defines a plane, and wherein the channel extends parallel to the plane.

39. The device of any of paragraphs 36 to 38, wherein the channel has a diameter of less than one millimeter.

40. The device of any of paragraphs 2 to 39, wherein the holder includes a channel junction that forms a droplet generator, and wherein the well communicates with the channel junction.

41. The device of any of paragraphs 2 to 40, wherein the holder defines a second well interconnected with the first well via one or more channels.

42. The device of any of paragraphs 2 to 41, wherein the holder includes a plurality of wells each having a protrusion that promotes wicking.

43. The device of paragraph 42, wherein the holder provides a plurality of emulsion production units each including at least one of the plurality of wells.

44. The device of any of paragraphs 1 to 41, wherein the well has a fluid capacity of less than about 100 microliters.

45. A method of using the device of any of paragraphs 1 to 44, comprising: dispensing an aqueous sample into the well.

46. The method of paragraph 45, wherein the aqueous sample has a contact angle with the side wall of greater than about 70 degrees.

47. The method of paragraph 45 or 46, wherein the Bond number for the aqueous sample in the well is <0.5 or <0.1.

48. The method of any of paragraphs 45 to 47, wherein less than about 50 microliters of the aqueous sample is dispensed into the well.

49. The method of any of paragraphs 45 to 48, wherein the holder defines a channel that communicates with the lower region of the well, and wherein at least a portion of the aqueous sample wicks into the channel from the well via the protrusion.

50. The method of any of paragraphs 45 to 49, further comprising a step of applying positive pressure and/or negative pressure to the aqueous sample after the step of dispensing, to drive the aqueous sample through a channel that communicates with the lower region of the well.

51. A method of making a device for holding a sample, the method comprising: (A) providing an upper member defining at least one through-hole having a surface forming a convex corner that extends about a central axis of the through-hole and that conceptually divides the through-hole into an upper region and a lower region; and (B) creating a well having a lower member attached to an underside of the upper member, with the surface of the through-hole forming a side wall of the well and the lower member forming a floor of the well, wherein the upper member, the lower member, or both the upper member and the lower member collectively, define a protrusion adapted to promote wicking of a fluid sample into the lower region from the upper region.

52. The method of paragraph 51, wherein the step of providing includes a step of molding the upper member.

53. The method of paragraph 51 or 52, wherein the convex corner extends completely around the central axis.

54. The method of any of paragraphs 51 to 53, wherein the step of creating a well includes a step of attaching the lower member to the upper member.

55. The method of paragraph 54, further comprising a step of deforming the lower member before, during, and/or after the step of attaching to define the protrusion.

56. The method of paragraph 55, wherein the step of deforming creates a dimple in a bottom surface of the lower member.

57. The method of paragraph 55 or 56, wherein the step of deforming creates a plurality of dimples in parallel, with each dimple being aligned with a different well.

58. The method of any of paragraphs 55 to 57, wherein the step of deforming includes a step of heating the lower member and a step of applying pressure to the lower member.

59. The method of paragraph 58, wherein the step of heating and the step of applying pressure are performed with a same tool.

60. The method of paragraph 54, wherein the protrusion is defined by the lower member before the step of attaching.

61. The method of paragraph 51, wherein the protrusion is integral to the upper member.

62. The method of any of paragraphs 51 to 61, wherein the step of providing includes a step of molding the upper member with a mold including a first die member having a pin and a second die member having a pad, and wherein the pin and the pad are engaged with each other in the mold and collectively create the through-hole.

63. The method of paragraph 62, wherein the pin has a tip diameter, and wherein a diameter of the pad is greater than the tip diameter such that the convex corner is formed at a junction of the pin and the pad.

64. The method of paragraph 62 or 63, wherein the pad defines a recess that generates the protrusion when the upper member is produced.

65. The method of any of paragraphs 51 to 64, further comprising a step of attaching the upper and lower members to each other, wherein the step of attaching creates a channel that is collectively bounded by the upper member and the lower member and that communicates with the lower region of the well.

66. The method of any of paragraphs 51 to 65, wherein the step of providing includes a step of injection molding an upper member that includes the protrusion.

67. The method of any of paragraphs 51 to 66, wherein the upper member has a plurality of through-holes, and wherein the upper member attached to the lower member creates a well from each through-hole.

68. The method of any of paragraphs 51 to 67, wherein each of the upper and lower members is composed of a polymer.

69. The method of paragraph 51, wherein the lower member includes a sheet member and a protrusion member, further comprising a step of attaching the protrusion member to, or forming the protrusion member on, a top surface of the sheet member.

70. The method of paragraph 69, wherein the protrusion member is attached to the sheet member by solvent bonding, thermal bonding, glue bonding, a mechanical connection, or a combination thereof.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and sub-combinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A device for holding a sample, comprising:
   a holder including an upper member attached to a lower member to form a well having a side wall region and a floor, the side wall region extending from a top border to the floor and widening toward the floor at a position intermediate the top border and the floor to create a distinct edge that conceptually divides the well into an upper portion and a lower portion, the well including a side wall protrusion defined by the upper member and adapted to promote wicking of an aqueous sample into the lower portion from the upper portion, the holder defining a channel communicating with the lower portion of the well and with a channel junction that provides a droplet generator;
   wherein the side wall protrusion is contiguous with the edge.

2. The device of claim 1, wherein a top of the side wall protrusion is disposed at a same elevation as the edge.

3. The device of claim 1, wherein the side wall protrusion abuts the lower member.

4. The device of claim 1, wherein the side wall protrusion is spaced from the lower member to form a gap between the protrusion and the lower member.

5. The device of claim 1, wherein the side wall protrusion projects at least generally toward a central vertical axis of the well from the side wall region.

6. The device of claim 1, wherein the holder includes a plurality of wells each having a protrusion that promotes wicking, and wherein the holder provides a plurality of emulsion production units each including at least one of the plurality of wells.

7. A device for holding a sample, comprising:
   a holder including an upper member attached to a lower member to form a well having a side wall region and a floor, the side wall region extending from a top border to the floor and widening toward the floor at a position intermediate the top border and the floor to create a distinct edge that conceptually divides the well into an upper portion and a lower portion, the floor defining a protrusion projecting upwardly in the well, the holder defining a channel communicating with the lower portion of the well;
   wherein the lower member defines a recess under the protrusion.

8. The device of claim 7, wherein the lower member is a sheet member having a top surface and a bottom surface, and wherein the sheet member is deformed such that the top surface defines the protrusion and the bottom surface defines the recess.

9. A method of making a device for holding a sample, the method comprising:
   providing an upper member defining at least one through-hole bounded by a side wall region, the side wall region extending from a top border to a bottom border and widening toward the bottom border at a position intermediate the top border and the bottom border to create a distinct edge that conceptually divides the through-hole into an upper portion and a lower portion;
   attaching a lower member to an underside of the upper member to create a well bounded laterally by the side wall region and having a floor formed by the lower member; and
   deforming the lower member to define a protrusion adapted to promote wicking of an aqueous sample into the lower portion from the upper portion.

10. The method of claim 9, wherein the step of attaching creates a plurality of wells, and wherein the step of deforming creates a plurality of recesses in a bottom surface of the lower member, with each recess being aligned with a different well.

11. The method of claim 9, wherein the step of deforming includes a step of heating the lower member and a step of applying pressure to the lower member, and wherein the step of heating and the step of applying pressure are performed with a same tool.

12. A device for holding a sample, comprising:
   a holder including an upper member attached to a lower member to form a well having a side wall region and a floor, the side wall region extending from a top border to the floor and widening toward the floor at a position intermediate the top border and the floor to create a distinct edge that conceptually divides the well into an upper portion and a lower portion, the floor defining a protrusion projecting upwardly into the upper portion of the well, the holder defining a channel communicating with the lower portion of the well.

13. The device of claim 12, wherein a bottom surface region of the lower member under the protrusion is flat.

14. The device of claim 12, wherein the channel communicates with at least one other well of the holder.

* * * * *